United States Patent
Werahera et al.

(10) Patent No.: US 9,814,448 B2
(45) Date of Patent: Nov. 14, 2017

(54) THREE-DIMENSIONAL OPTICAL IMAGING AND THERAPY OF PROSTATE CANCER

(71) Applicants: The Regents of the University of Colorado, a body corporate, Denver, CO (US); Precision Biopsy, LLC, Aurora, CO (US)

(72) Inventors: Priya N. Werahera, Aurora, CO (US); Amir Tehrani, San Francisco, CA (US); Edward Jasion, Denver, CO (US)

(73) Assignee: Precision Biopsy, Inc., Boston, MA (US)

( * ) Notice: Subject to any disclaimer, the term of this patent is extended or adjusted under 35 U.S.C. 154(b) by 0 days.

(21) Appl. No.: 14/400,942

(22) PCT Filed: May 20, 2013

(86) PCT No.: PCT/US2013/041858
§ 371 (c)(1),
(2) Date: Nov. 13, 2014

(87) PCT Pub. No.: WO2013/177061
PCT Pub. Date: Nov. 28, 2013

(65) Prior Publication Data
US 2015/0150459 A1 Jun. 4, 2015

Related U.S. Application Data

(63) Continuation-in-part of application No. 13/898,062, filed on May 20, 2013.
(Continued)

(51) Int. Cl.
*A61B 5/00* (2006.01)
*A61B 5/055* (2006.01)
(Continued)

(52) U.S. Cl.
CPC ............ *A61B 10/04* (2013.01); *A61B 1/0016* (2013.01); *A61B 1/043* (2013.01); *A61B 1/0684* (2013.01);
(Continued)

(58) Field of Classification Search
CPC ......... A61B 18/02; A61B 18/12; A61B 18/20; A61B 2018/048; A61B 2562/046;
(Continued)

(56) References Cited

U.S. PATENT DOCUMENTS

| 4,930,516 A | 6/1990 | Alfano et al. |
| 5,042,494 A | 8/1991 | Alfano |

(Continued)

FOREIGN PATENT DOCUMENTS

| EP | 1559363 A2 | 8/2005 |
| WO | 96/03923 A1 | 2/1996 |

(Continued)

OTHER PUBLICATIONS

Bigio, Irving J. et al., Ultraviolet and visible spectroscopies for tissue diagnostics: fluorescence spectroscopy and elastic-scattering spectroscopy, Phys. Med. Biol. 42 (1997) 803-814.
(Continued)

*Primary Examiner* — Michael Rozanski
(74) *Attorney, Agent, or Firm* — Senniger Powers LLP

(57) ABSTRACT

A system, method, and storage device storing computer executable instructions for use in tissue analysis and therapy. An optical probe array has at least two or more optical probes for illuminating tissue and generates light fluorescence and/or diffuse reflectance signals corresponding to the illuminated tissue. One or more ultrasound, CT and MRI imaging guidance systems identify the position of the optical probes relative to the tissue. The imaging guidance system can also be a fusion of an MRI or CT image provided by the
(Continued)

MRI or CT imaging guidance system and an ultrasound image provided by the ultrasound imaging guidance system. An imaging system generates a three-dimensional image of the tissue based on the generated light signals and the identified position of the optical probes.

33 Claims, 26 Drawing Sheets

Related U.S. Application Data

(60) Provisional application No. 61/649,694, filed on May 21, 2012.

(51) Int. Cl.

| | | |
|---|---|---|
| A61B 6/03 | (2006.01) | |
| A61B 8/08 | (2006.01) | |
| A61B 10/04 | (2006.01) | |
| A61B 5/06 | (2006.01) | |
| A61B 1/00 | (2006.01) | |
| A61B 1/06 | (2006.01) | |
| A61B 1/07 | (2006.01) | |
| A61B 8/12 | (2006.01) | |
| A61B 8/00 | (2006.01) | |
| A61B 1/04 | (2006.01) | |
| A61B 6/12 | (2006.01) | |
| A61B 10/02 | (2006.01) | |
| A61N 5/06 | (2006.01) | |
| A61N 5/10 | (2006.01) | |
| A61B 18/04 | (2006.01) | |
| A61B 34/20 | (2016.01) | |
| A61B 17/34 | (2006.01) | |
| A61B 1/307 | (2006.01) | |
| A61N 7/02 | (2006.01) | |
| A61B 18/14 | (2006.01) | |
| A61B 18/22 | (2006.01) | |
| A61B 18/02 | (2006.01) | |
| A61B 90/00 | (2016.01) | |
| A61B 90/30 | (2016.01) | |

(52) U.S. Cl.
CPC .............. *A61B 1/07* (2013.01); *A61B 5/0035* (2013.01); *A61B 5/0071* (2013.01); *A61B 5/0075* (2013.01); *A61B 5/0084* (2013.01); *A61B 5/061* (2013.01); *A61B 5/4836* (2013.01); *A61B 5/6848* (2013.01); *A61B 6/12* (2013.01); *A61B 8/0841* (2013.01); *A61B 8/12* (2013.01); *A61B 8/461* (2013.01); *A61B 10/0241* (2013.01); *A61B 1/0638* (2013.01); *A61B 1/307* (2013.01); *A61B 5/6835* (2013.01); *A61B 6/032* (2013.01); *A61B 18/1477* (2013.01); *A61B 18/22* (2013.01); *A61B 2010/045* (2013.01); *A61B 2017/3413* (2013.01); *A61B 2018/0293* (2013.01); *A61B 2018/048* (2013.01); *A61B 2034/2055* (2016.02); *A61B 2034/2063* (2016.02); *A61B 2090/309* (2016.02); *A61B 2090/364* (2016.02); *A61B 2090/3614* (2016.02); *A61B 2090/3782* (2016.02); *A61B 2562/046* (2013.01); *A61N 5/062* (2013.01); *A61N 5/1001* (2013.01); *A61N 5/1027* (2013.01); *A61N 7/022* (2013.01); *A61N 2005/0612* (2013.01)

(58) Field of Classification Search
CPC ... A61B 5/0035; A61B 5/0071; A61B 5/0075; A61B 5/0084; A61B 5/061; A61B 5/4836; A61B 5/6835; A61B 5/6848; A61B 6/03; A61B 8/0841; A61N 5/062; A61N 5/1001; A61N 7/02
See application file for complete search history.

(56) References Cited

U.S. PATENT DOCUMENTS

| | | |
|---|---|---|
| 5,131,398 A | 7/1992 | Alfano et al. |
| 5,280,788 A | 1/1994 | Janes et al. |
| 5,368,045 A | 11/1994 | Clement et al. |
| 5,983,125 A | 11/1999 | Alfano et al. |
| 6,124,358 A | 9/2000 | Estanove et al. |
| 6,167,297 A | 12/2000 | Benaron |
| 6,174,291 B1 | 1/2001 | McMahon et al. |
| 6,205,353 B1 | 3/2001 | Alfano et al. |
| 6,405,074 B1 | 6/2002 | Banerjee |
| 6,485,413 B1 | 11/2002 | Boppart et al. |
| 6,564,087 B1 | 5/2003 | Pitris et al. |
| 6,760,613 B2 | 7/2004 | Nordstrom et al. |
| 8,406,858 B2 | 3/2013 | Werahera et al. |
| 2002/0026127 A1 | 2/2002 | Balbierz et al. |
| 2002/0082518 A1 | 6/2002 | Weiss et al. |
| 2002/0143243 A1 | 10/2002 | Georgakoudi et al. |
| 2003/0041041 A1 | 2/2003 | Cristianini |
| 2003/0055341 A1 | 3/2003 | Banerjee |
| 2003/0135122 A1 | 7/2003 | Bambot et al. |
| 2003/0162301 A1 | 8/2003 | Noergaard et al. |
| 2006/0139633 A1 | 6/2006 | Puppels et al. |
| 2006/0173359 A1 | 8/2006 | Lin et al. |
| 2007/0075226 A1 | 4/2007 | Engstrand |
| 2008/0194969 A1 | 8/2008 | Werahera et al. |
| 2010/0198080 A1 | 8/2010 | Liu et al. |
| 2010/0228238 A1 | 9/2010 | Brennan et al. |
| 2010/0331782 A1* | 12/2010 | Hendriks ............ A61B 5/0066 604/164.12 |
| 2011/0319759 A1 | 12/2011 | Liu et al. |
| 2012/0071749 A1 | 3/2012 | Xu et al. |
| 2012/0245473 A1 | 9/2012 | Mycek et al. |
| 2013/0310680 A1* | 11/2013 | Werahera ............ A61B 5/0035 600/411 |
| 2014/0213911 A1 | 7/2014 | Bierhoff et al. |

FOREIGN PATENT DOCUMENTS

| | | |
|---|---|---|
| WO | 98/27965 | 7/1998 |
| WO | 2004/041060 A3 | 5/2004 |
| WO | 2005/092194 A1 | 10/2005 |
| WO | 2006/119166 A2 | 11/2006 |
| WO | 2009/109873 A1 | 9/2009 |
| WO | 2009/144653 A2 | 12/2009 |
| WO | 2011066149 A1 | 6/2011 |
| WO | 2011093108 A1 | 8/2011 |

OTHER PUBLICATIONS

Crawford, E. David et al., Clinical staging of prostate cancer: a computer-simulated study of transperineal prostate biopsy, (2005) BJU International 96, 999-1004.

Palmer, Gregory M. et al., Autofluorescence Spectroscopy of Normal and Malignant Human Breast Cell Lines, Photochemistry and Photobiology, 2003, 78(5), 462-469.

Palmer, Gregory M. et al., Comparison of Multiexcitation Fluorescence and Diffuse Reflectance Spectroscopy for the Diagnosis of Breast Cancer, IEEE Transactions on Biomedical Engineering, vol. 50, No. 11, Nov. 2003, pp. 1233-1242.

Ramanujam, Nirmala, Fluorescence Spectroscopy of Neoplastic and Non-Neoplastic Tissues, Neoplasia, vol. 2, Nos. 1-2, Jan.-Apr. 2000, pp. 89-117.

Utzinger, Urs et al., Fiber optic probes for biomedical optical spectroscopy, Journal of Biomedical Optics, Jan. 2003, vol. 8, No. 1, pp. 121-147.

Werahera, Priya N. et al., Biomorphometric Analysis of Human Prostatic Carcinoma by Using Three-Dimensional Computer Models, Human Pathology, vol. 35, No. 7 (Jul. 2004), pp. 798-807.

(56) References Cited

OTHER PUBLICATIONS

Crawford, E. David et al., Computer Modeling of Prostate Biopsy: Tumor Size and Location—Not Clinical Significance—Determine Cancer Detection, The Journal of Urology, vol. 159, pp. 1260-1264 (Apr. 1998).

Kuo, Wei-Cheng et al., Real-time three-dimensional optical coherence tomography image-guided core-needle biopsy system, Biomedical Optics Express, vol. 3, No. 6, Jun. 1, 2012, pp. 1149-1161.

Peikari, Mohammad et al, Characterization of ultrasound elevation beamwidth artifacts for prostate brachytherapy needle insertion, Medical Physics, vol. 39, No. 1, Jan. 2012, pp. 246-256.

Extended European Search Report dated Jan. 27, 2016 relating to European Patent Application No. 13794535.8, 14 pages.

International Search Report dated Sep. 28, 2016 relating to PCT Patent Application No. PCT/US2016/041225, 3 pages.

\* cited by examiner

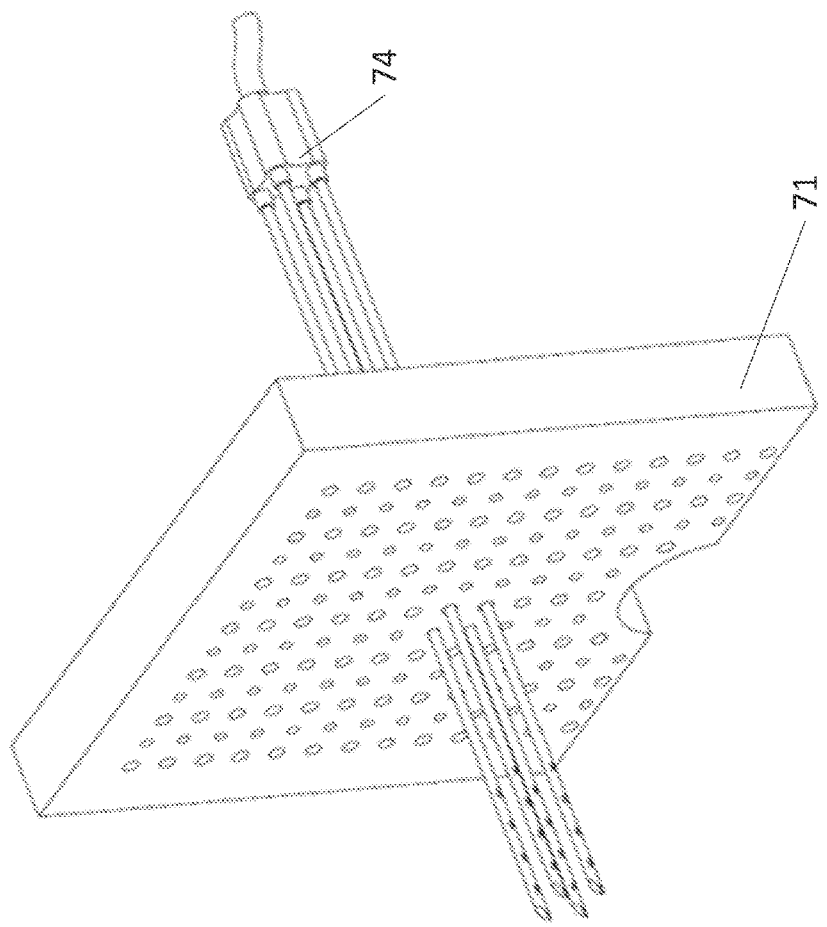
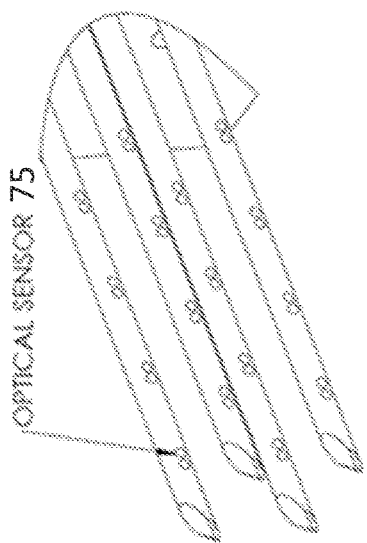
FIG. 8

THREE-DIMENSIONAL OPTICAL IMAGING AND THERAPY OF PROSTATE CANCER

REFERENCE TO RELATED APPLICATIONS

This application is a U.S. national stage application of International Patent Application No. PCT/US2013/041858, filed May 20, 2013, which claims the benefit of U.S. Provisional Application No. 61/649,694, filed May 21, 2012, the entire disclosures of which are incorporated herein by reference. This application is also a U.S. Continuation-in-Part of U.S. application Ser. No. 13/898,062 filed on May 20, 2013, which claims the benefit of U.S. Provisional Application No. 61/649,694, filed May 21, 2012, the entire disclosures of which are incorporated herein by reference.

BACKGROUND

The American Cancer Society estimates that in the United States in 2013, 238,590 new cases of prostate cancer (PCa) will be diagnosed compared with approximately 99,000 cases diagnosed in 1988 attributable to the advent of prostate-specific antigen (PSA) screening. Consequently, there has been stage migration with earlier stage at diagnosis. Presently, 92% of incident PCa are locoregional versus metastatic. Hence, only 29,720 men are estimated to die from this disease in 2013. Accurate staging before treatment is desirable given the relatively high number of men who must be treated to prevent PCa-specific death. PCa has a long latency period and consequently more men die with rather than from this disease. Hence, a significant proportion of US men with localized PCa are overdiagnosed and overtreated with attendant morbidity and significant cost escalations as insignificant tumors were detected via aggressive screening procedures.

Transrectal ultrasound (TRUS) guided tissue biopsy of the prostate is the current method of screening for PCa. Pathological examination of tissue needs to confirm the presence of the disease. However, prostate biopsies are subjected to serious sampling errors and frequently miss aggressive PCa that warrant definitive therapy during initial screenings. The PCa detection rate according to the current standard of care for TRUS-guided needle biopsies with 10-12 biopsy cores is only 25-30%, while more than 50% of cancers that require definitive treatment remain undetected during initial biopsies. Such undetected cancers due to false negative biopsies are at risk of spreading beyond the prostate gland and metastasizing to distant sites. Even when PCa were diagnosed by prostate biopsies, they may fail to provide accurate information regarding histologic grade and stage of the disease that are needed for therapeutic decisions. Aggressive PCa lesions may be differentiated from non-aggressive or latent PCa based on histologic grade, pathologic stage, and volume. Aggressive PCa for organ-confined disease may be defined as those tumors with volume ≥0.5 cc or Gleason[8] sum≥7.

SUMMARY

In one form, a system is provided for use with a tissue. An optical probe array has at least two or more optical probes for illuminating the tissue and generates light signals corresponding to the illuminated tissue. An imaging system generates an image of the tissue based on the generated light signals and the identified position of the optical probes.

In another form, a probe array is provided for use with a tissue. The array comprises a plurality of optical probes, each optical probe comprising a shaft, and two or more optical devices supported by the shaft, each for illuminating the tissue adjacent its shaft and for detecting light adjacent to its shaft from the illuminated tissue.

In another form, a method comprises:
positioning two or more optical light sources adjacent to or within tissue to illuminate the tissue;
capturing spectra or other optical phenomena from the illuminated tissue using a sensor;
characterizing the tissue at the location of the optical sensor based on the captured spectra or other optical phenomena and determining corresponding coordinates of the tissue to map a 3D image of the tissue; and
creating the 3D optical image of the tissue based on the mapped 3D image.

In another form, a tangible, non-transitory storage medium device stores computer executable instructions executable by a processor to validate data indicative of tissue and based on a support vector machine (SVM) or other statistical methods and systems suitable for classification such as linear discriminant analysis (LDA), artificial neural networks (ANN), multiple logistic regression, etc. The device includes instructions for:
collecting raw data of the tissue;
conditioning of the raw data;
preprocessing of the conditioned data;
evaluating the preprocessed data for prostate cancer;
identifying prostate cancer from the evaluated data; and
validating the identified data.

In another form, a system is provided for use with a tissue. An optical probe array has at least two or more optical probes for illuminating the tissue and generates light signals corresponding to the illuminated tissue fluorescence and/or corresponding to the illuminated tissue diffuse reflectance spectroscopy for distinguishing between cancer tissue and non-cancer tissue. An MRI or CT imaging guidance system identifies the position of the optical probes relative to the tissue. An ultrasound imaging guidance system identifies the position of the optical probes relative to the tissue. A three-dimensional user interface imaging system generates a three-dimensional image of the tissue based on the generated light signals and the identified position of the optical probes as indicated by the MRI or CT imaging guidance system and as indicated by the ultrasound imaging guidance system. The image is a fusion of an MRI or CT image provided by the MRI or CT imaging guidance system and an ultrasound image provided by the ultrasound imaging guidance system.

BRIEF DESCRIPTION OF THE DRAWINGS

FIG. 1 is schematic representation of a transverse view plus ultrasound image of an array of cryoneedles, and FIG. 2 is an ultrasound image of a longitudinal view of FIG. 1 showing an array of cryoneedles (striated).

FIG. 5B is provided to illustrate some of the details of FIG. 5A.

FIG. 8 illustrates a 2×2 fiber optic probe array with optical sensors on the left side and the 2×2 fiber optic probe array with optical sensors in combination with a brachytherapy template or similar on the right according to one embodiment.

FIG. 24 also illustrates one photograph 340A on the left side which illustrates elastic scattering spectra captured from the location or vicinity of the cancer lesion shown in MRI/US fusion image. When this spectrum is processed by a tissue classification algorithm, it can either confirm or contradict the existence of cancer lesion shown in MRI/US fusion image for 3D optical mapping of the prostate.

FIG. 25 also illustrates one photograph 340B on the left side which illustrates fluorescence spectra captured from the location or vicinity of the cancer lesion shown in MRI/US fusion image 343C. When the spectra is processed by a tissue classification algorithm, it can either confirm or contradict the existence of cancer lesion shown in MRI/US fusion image for 3D optical mapping of the prostate.

DETAILED DESCRIPTION

Figure 1:
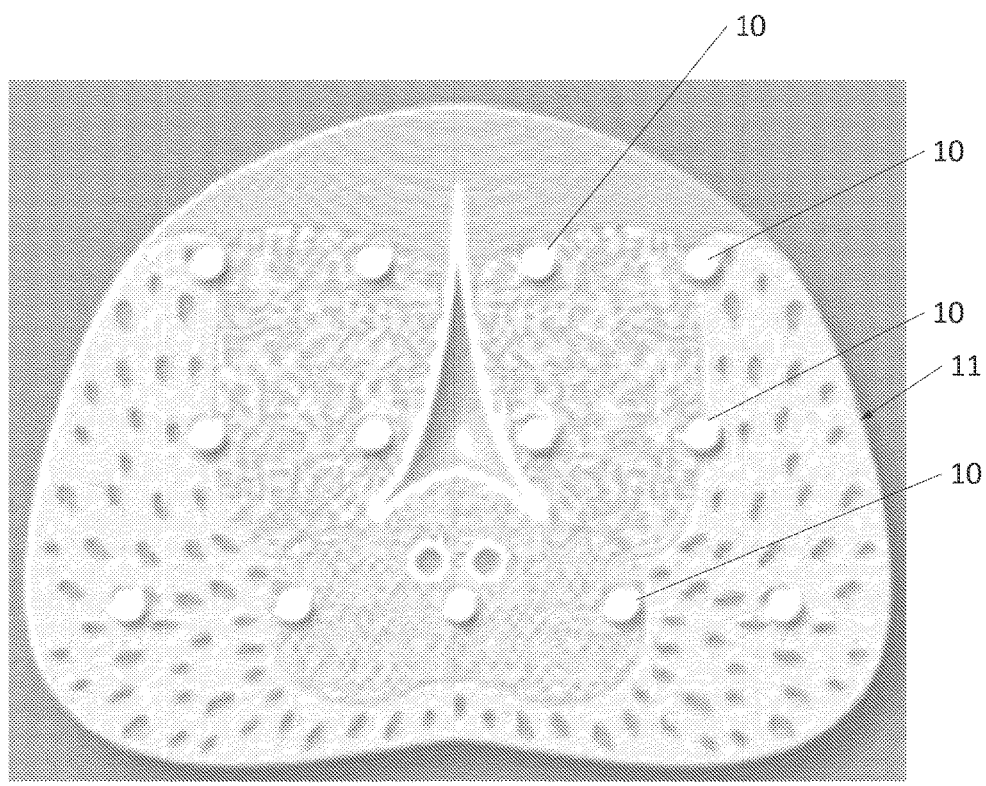
FIGS. 1 and 2 illustrate positioning of the cryoneedles within prostate tissue for either whole-gland therapy or focal therapy purposes.

An optical probe array (e.g., a needle having an integrated optical sensor at its tip) is used in combination with an image guiding system (e.g., an ultrasound system) and/or in combination with an imaging system (e.g., fluorescence and/or diffuse reflectance spectroscopy) to obtain in vivo optical spectroscopically-guided prostate analysis and/or treatment. This enables one to sample and diagnostically classify different types of tissue within the prostate. The optical probes interface with a device, such as a fluorometer or fluorescence spectroscope, used to measure light parameters, such as fluorescence. In one embodiment, software to control a fluorometer, an optical data acquisition device, a user interface, and a tissue classification system resides on a laptop computer. In one configuration, the fluorometer comprises two light sources with peak emissions respectively at 290 and 340 nm, one broadband light source 500-1000 nm and a spectrometer (e.g., CCD-based (charge coupled device), PMT-based (photon multiplier tube), etc.). Systematic application of this technology uses optical measurements to indicate presence of cancer within the prostate permitting determination of highest histologic grade and stage of the disease at the time of biopsy and permitting targeted treatment. In addition, based on the number of positive cores and percentage core involvement, embodiments provide information regarding size (volume), location, and distribution of PCa. In at least some situations this information can be combined to determine if a patient has aggressive disease or not and hence to customize therapeutic options to meet the needs of each patient.

Embodiments significantly improve diagnosis, staging, and therapy of PCa involving the following: 1) Accurate diagnosis and localization of PCa lesions using a TRUS-guided standard biopsy, saturation biopsy, or brachytherapy template-guided mapping biopsy using optical biopsy needle and associated technology, 2) Determine whether patient has aggressive PCa based on histopathological grade, pathologic stage, number of positive cores, and percentage core involvement, 3) Personalized therapy and when applicable adjunct with an optical probe and associated technology, and 4) Monitor response during therapy and progress following therapy. Based on histopathological findings from biopsy tissue, patients with aggressive PCa lesions that require definitive, potentially curative treatment which may include surgery, radiation, and neoadjuvant therapy can be identified. The aim of neoadjuvant therapy is to maximize cure rates for patients who have undergone definitive therapy for localized disease, theoretically by eliminating micrometastatic disease. Patients assessed to have non-aggressive disease may be candidates for watchful-waiting (WW) or active surveillance (AS). We believe this approach is a vital step to minimize overtreatment of PCa according to the current standard of care since 5 out of 6 men diagnosed with PCa may be candidates for WW or AS. It will also lead to early diagnosis of clinically important cancer and gives an opportunity to intervene where therapy benefits the patient.

Figure 2:
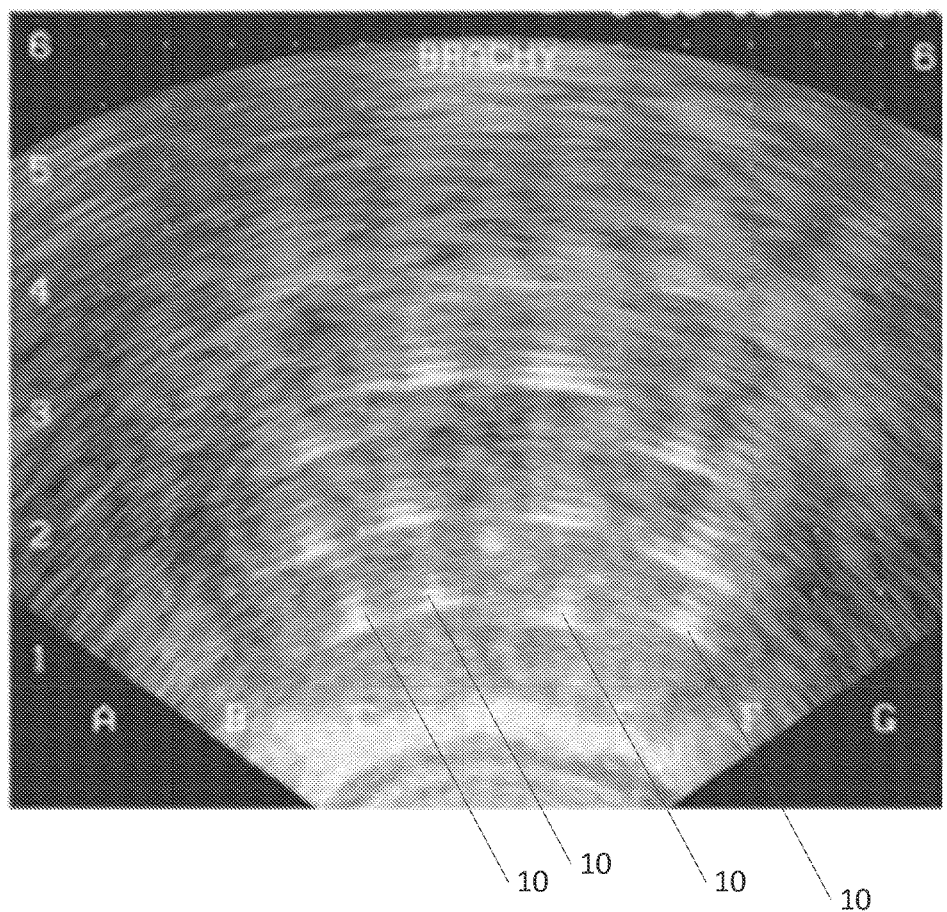

Definitive whole-gland therapy for PCa has serious side effects including erectile dysfunction (ED) and urinary incontinence. The concept of "highly selective" ablative procedures or targeted focal therapy (TFT) for PCa is being considered in certain low-risk patients. During TFT, therapeutic agent is targeted directly onto each PCa lesion or regions within the prostate instead of the entire gland. This option would hypothetically result in a significant decrease in the morbidity associated with PCa treatment, particularly ED. The process of TFT includes careful three-dimensional (3D) mapping of PCa lesions within the prostate gland followed by focused targeted treatment to only those lesions or regions where PCa lesions are located. However, screening patients for this procedure is a challenge. Further, guiding treatment based on TRUS-guided biopsy findings is difficult due to prostate movement and deformation or warping. Using 3D computer models of autopsy prostates with previously undetected carcinomas, it has been proven that transperineal mapping biopsy (TMB) as the method to identify patients with low-risk PCa for TFT (e.g., positioning of cryoneedles 10 within prostate tissue 11 following transperineal mapping biopsy procedure). FIG. 1 is schematic representation of a transverse view, and FIG. 2 is an ultrasound image of a longitudinal view of an array of cryoneedles (striated) 10.

In one embodiment, a 5-mm grid transperineal mapping biopsy consistently sampled the highest Gleason grade 4/5 tumors and detected aggressive PCa with sensitivity, specificity, positive predictive value (PPV), and negative predictive value (NPV) of 95%, 30%, 31%, and 95%, respectively. Specificity and positive predictive value were lower since the transperineal mapping biopsy detected a higher proportion of clinically insignificant PCa lesions.

By combining an optical biopsy needle and/or an optical probe with transperineal mapping biopsy, similar diagnostic information regarding tumor locations and tumor distribution can be obtained enabling therapeutic agents to be directed to these same locations for targeted focal therapy (TFT). This document describes diagnostic and therapeutic modalities based on the optical probe and associated technologies for TFT for low risk PCa cancer patients sparing them serious side-effects associated with definitive therapies such as surgery and radiation.

Therapeutic Modalities

Cryotherapy:

Cryoablation of the prostate may be used to treat localized prostate cancer or recurrences after previous treatments. Cryoablation of the prostate may be done through total freezing of the prostate. Alternatively, cryoablation may be restricted to focal or regional freezing to treat only the involved areas of the prostate as in TFT. In this manner the nerves for erection sitting on the uninvolved part of the prostate may remain intact to preserve erections. Cryotherapy has been performed worldwide for over 50 years. The American and European Association of Urology guidelines on prostate cancer state that cryotherapy is a true therapeutic alternative for patients with clinically localized prostate cancer. The American Association of Urology recently made an announcement of a best practice statement confirming cryotherapy as a valid treatment option for both primary and recurrent localized prostate cancer. In 2005 in the UK, the National Institute of Clinical Excellence approved the use of cryotherapy for patients with prostate cancer, both as a primary treatment and as salvage treatment after radiotherapy or hormone therapy.

Cryotherapy causes cell death through two principle mechanisms. First, as the temperature falls, extracellular ice crystallizes causing movement of water from the intracellular to the extracellular environment after an osmotic gradient. As the temperature continues to fall, intracellular ice crystals form, causing direct damage to the intracellular organelle system and the cell membrane. The second mechanism is platelet aggregation and microthrombus formation in small blood vessels, which leads to ischemic change in the tissue area supplied by the affected blood vessels. These changes lead to coagulative necrosis and cause a well demarcated lesion. In addition, severe temperature changes and ischemic change induce apoptosis in cells at the periphery of the cryolesion.

The effectiveness of the cellular destruction depends on rapid freezing, the lowest temperature reached and slow thawing. This is generally achieved through two freeze-thaw cycles to a target temperature of −40° C.

Cryoablation of prostate cancer first took place in 1968 using probes cooled by liquid nitrogen in a closed system. The early technique was associated with considerable complications, such as rectourethral fistulas, urethral sloughing and urinary incontinence. With the introduction of TRUS guidance and the urethral warming catheter, improved results have been achieved. The subsequent development of cryotherapy using 17-gauge needles with echogenic tips has allowed controlled and accurate delivery of the treatment. The current system uses high-pressure argon and helium gas for freezing and warming, respectively. The temperature change is governed by the Joule-Thompson effect, whereby high-pressure gases, when forced though a very small opening into a low-pressure area (within the tip of the cryoneedles), undergo specific temperature changes. This allows the freezing and subsequent thawing of the prostate using the same needle. During the treatment, the temperature in different areas of the prostate is monitored in real time by means of interstitial thermosensors. The needles are placed under TRUS guidance through the skin of the perineum using a brachytherapy template without the need for tract dilatation and with minimal trauma to the patient. As the gas is delivered through the specialized needles, it cools the prostate tissue rapidly to the target temperature of −40° C. The ice ball is clearly visible on TRUS as it forms and is monitored continuously throughout the procedure. The use of urethral warmer reduces the incidence of urethral sloughing.

Cryotherapy following 3-D mapping of PCa lesions using optical probes with optical sensors and associated system to treat tissue identified in a generated image as noted herein will allow accurate real-time reading and staging of the tumor, directing treatment to the areas affected by PCa (FIGS. 1-2). As noted above, FIGS. 1 and 2 illustrate positioning of the cryoneedles for whole-gland or focal therapy procedure. FIG. 1 is schematic representation of a transverse view plus ultrasound image, and FIG. 2 is an ultrasound image of a longitudinal view of the array of cryoneedles (striated) 10. It should be noted that prostate cancer localization and cryoablation or another form of therapy is not only limited to transperenial procedure. In some embodiments, a TRUS (transrectal ultrasound) system of cancer localization and immediate application of therapy through the mapping or biopsy needle or alternatively an independent catheter is contemplated.

Careful mapping of the prostate can be done using the brachytherapy grid that separates areas of the prostate by 0.5 cm allowing adequate therapeutic ice ball formation. The longitudinal area that will be surveyed by the optical probe will define every 0.5-1.7 cm the presence of PCa cells. The average prostate biopsy core is 1.7 cm and the average length of the prostate is approximately 4 cm.

Ultimately, biopsies will not be needed once correlation between PCa and optical probe is established, allowing intra-operative survey and assessment of tumors to be treated by cryoablation. The result of this work decreases the rate of complications or side effects due to cryotherapy, i.e.; erectile dysfunction, urinary incontinence and rectourethral fistula. TFT with recurrent treatment will be available allowing all procedures to be performed as outpatient basis increasing patient satisfaction and decrease cost of treatment.

Figure 3:
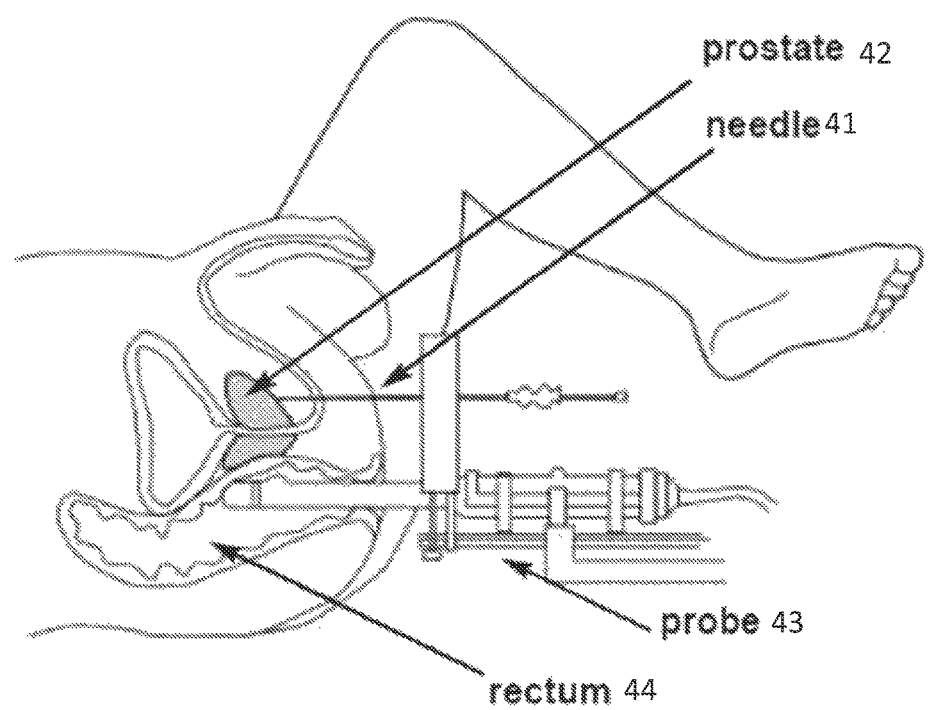
FIG. 3 illustrates strategic placement of a brachytherapy needle, such as to locate radioactive pellets within the prostate.
Figure 4:
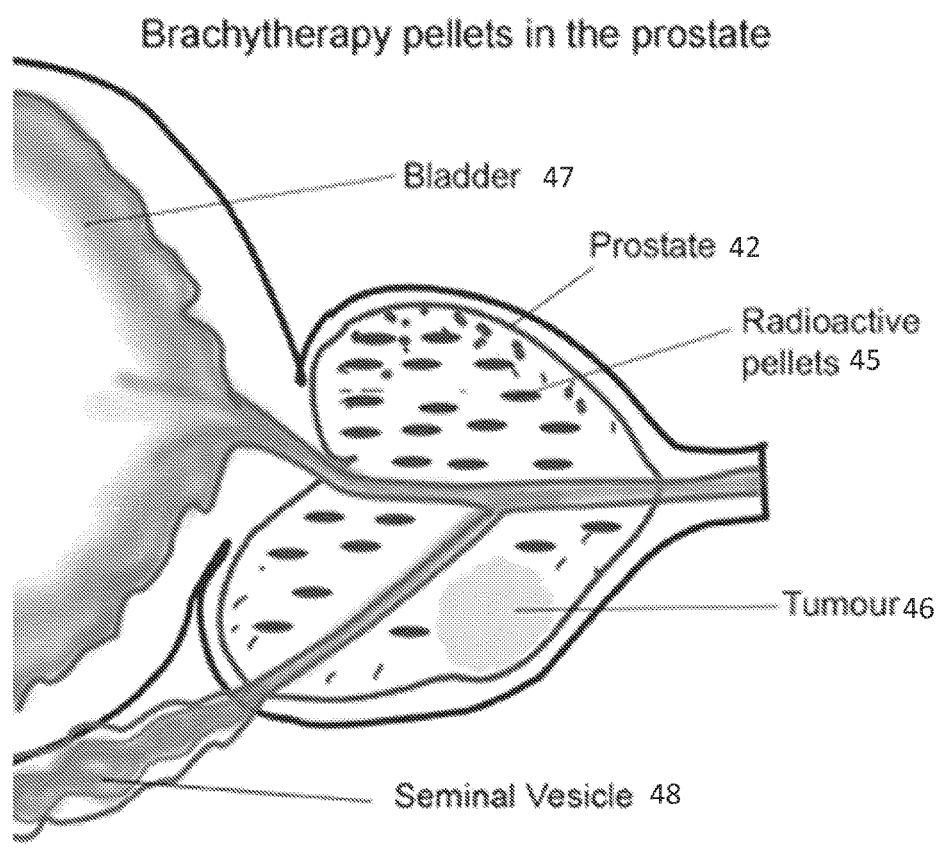
FIG. 4 illustrates brachytherapy in which radioactive pellets have been located within the prostate.

Optical probes will be placed in the prostate using the brachytherapy template. Following identification of tumors within the prostate, cryoprobes or brachytherapy needles with radioactive pellets are strategically placed for TFT applications (FIGS. 1-2 for cryotherapy and 3-4 for brachytherapy). For example, FIG. 1 may be a schematic representation of a transverse view plus ultrasound image of strategic placement of cryoprobes, and FIG. 2 is an ultrasound image of a longitudinal view of the array of cryoprobes (striated) 10. For example, FIG. 3 illustrates strategic placement of a brachytherapy needle 41 within a prostate 42, such as to locate radioactive pellets within the prostate 42, under the guidance of an ultrasound probe 43 within the rectum 44. FIG. 4 illustrates brachytherapy in which radioactive pellets 45 have been located within the prostate 42 about a tumor 46 relative to a bladder 47 and relative to a seminal vesicle 48.

Figure 5A:
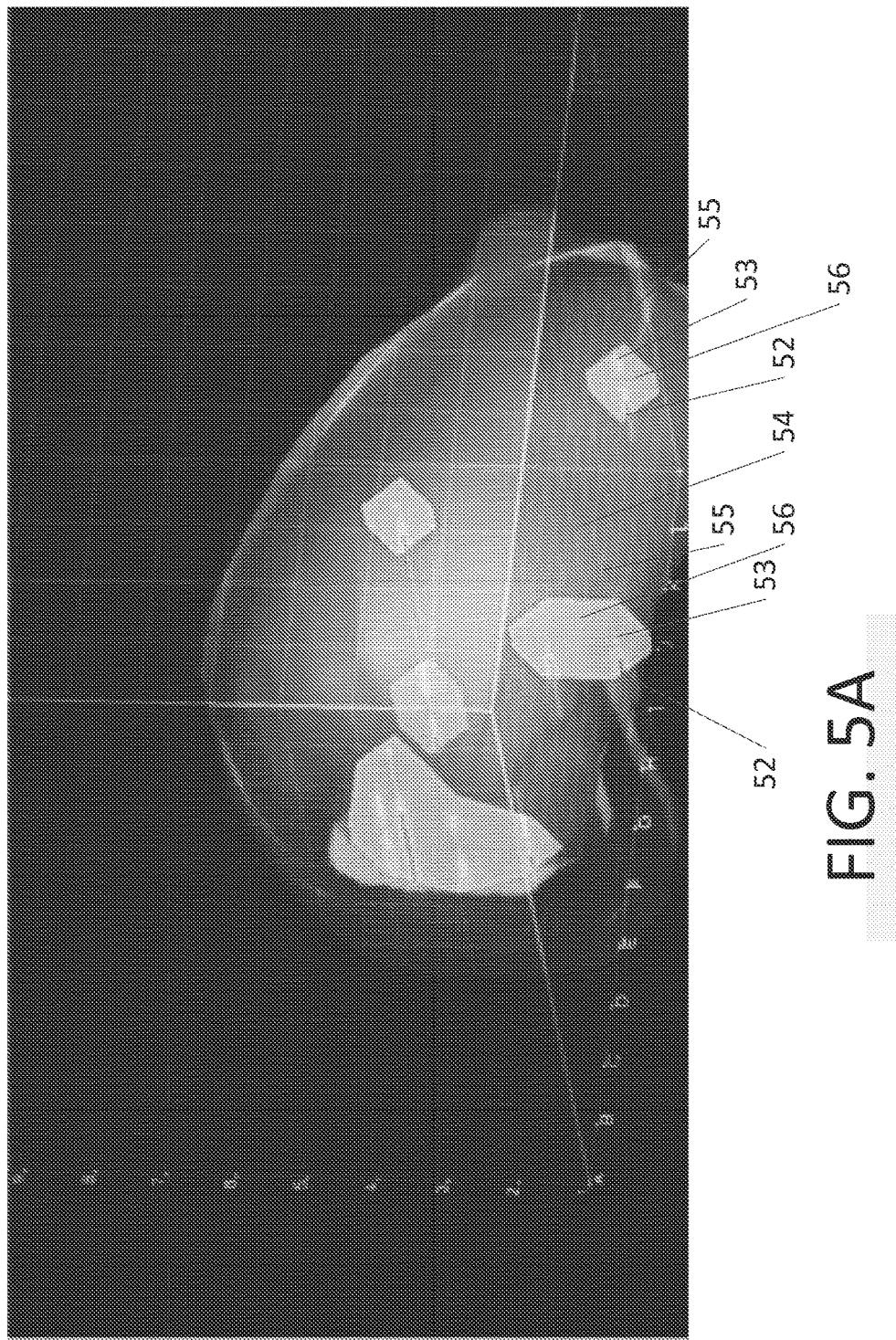
FIG. 5A illustrates a photograph of a three-dimensional (3D) optically mapped image of the prostate following optical measurements identifying locations of prostate cancer lesions according to one embodiment.
Figure 5B:
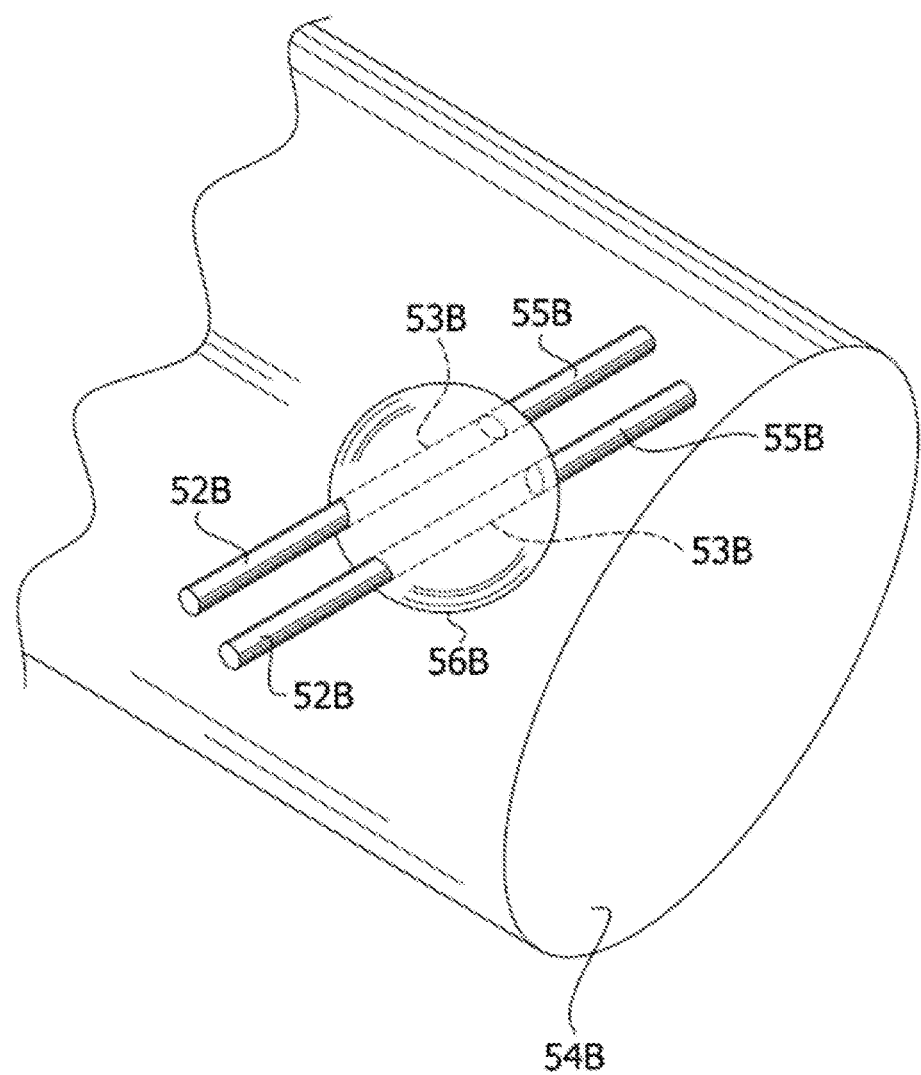
FIG. 5B corresponds to FIG. 5A and illustrates in a simplified line drawing of a perspective view of the three-dimensional (3D) optically mapped image of the prostate shown in FIG. 5A.

FIG. 5A illustrates a photograph of a three-dimensional (3D) optically mapped image of the prostate following optical measurements identifying locations of prostate cancer lesions according to one embodiment. FIG. 5B corresponds to FIG. 5A and illustrates in a simplified line drawing of a perspective view of the three-dimensional (3D) optically mapped image of the prostate shown in FIG. 5A; FIG. 5B is provided to illustrate some of the details of FIG. 5A.

FIG. 5A provides information which can serve as a precursor to a prostate biopsy or to guide therapy. In this context, optical biopsy needles (see needle tracks 52 which are on the near side of lesions 56, needle tracks 53 within the lesions 56, and needle tracks 55 on the far side of the lesions 56) are inserted in to a prostate gland 54 guided by a brachytherapy or another template. This template is located in transperineal direction and 5 mm and 10 mm or other grid points are provided for needle insertions. Optical spectroscopy measurements are obtained in discrete or continuous modes to detect cancer. Each grid coordinate and depth where lesions 56 are located will be recorded for therapeutic applications. Alternatively, lesions 56 may be treated as they are detected by laser ablation or photodynamic therapy using the optical biopsy needle 52.

In FIG. 5B, the partial cylinder 54B is intended to represent a portion of the prostate gland 54 shown in FIG. 5A. The sphere 56B is intended to represent the lesion 56 shown in FIG. 5A. The rods 52B represent the needle tracks 52 which are on the near side of lesion 56 shown in FIG. 5A. The rods 53B shown in phantom represent the needle tracks 53 which are within the lesion 56. The rods 55B represent the needle tracks 55 which are on the far side of lesion 56.

The whole prostate should be surveyed with the optical probe transversally and longitudinally using the TRUS probe in different views and detect continuous read from the optical sensors mounted on the optical probe. Pre-operative measurements of the prostate aid the placement of cryoneedles but also the previous biopsy report with histopathological data may help the surgeon concentrate attention in the areas proven to be positive for PCa.

Embodiments include several modifications to a needle (e.g., a biopsy needle) such as an optical probe with optical sensors, and associated technology to accommodate critical needs in cryotherapy applications including TFT. These embodiments will be discussed in further details herein.

1. Optical probe with multiple sensors separated by 5 mm or at greater or less spacing intervals.
2. Probe with either single or multiple sensors in motorized 2×2 or 3×3 configurations for transperineal forward/backward movement.
3. Optical needles in motorized 2×2 or 3×3 configurations for transperineal forward/backward movement.
4. Hardware and software modifications to fluorometer to accommodate configurations 1 and 2.
5. Above arrangement requires careful mapping of the prostate followed by cryoablation. Alternative configuration may be an integrated optical sensor and cryoneedle to concurrently achieve PCa diagnosis followed by cryoablation of those lesions.

Photodynamic Therapy:

Another minimally invasive treatment modality for PCa patients is photodynamic therapy (PDT). PDT is a treatment that uses photosensitizing drugs; these agents are pharmacologically inactive until they are exposed to near infrared (NIR) light in the presence of oxygen. The activated drug forms reactive oxygen species that are directly responsible for tissue destruction around the area exposed to NIR light. For PCa, the photosensitizers can be administered orally or intravenously, and are activated in the prostate by NIR light of a specific wavelength. This light is produced by a low-power laser or LED, and is delivered to the prostate using optical fibers within transparent plastic needles. The placement of the needles within the prostate is usually guided by transrectal ultrasound and brachytherapy template, and the procedure is normally performed under general anesthetic. Energy is either delivered via a cylindrical diffuser, which emits light along a length of fiber, or via a bare-tipped fiber, where the light comes out of the end only.

The photosensitizing drugs available vary in their modes of action. Some drugs are tissue-based photosensitizers, and take a number of days to reach maximal concentration in the target organ. These drugs tend to accumulate in the skin, where they can be activated by sunlight or artificial room light for a number of weeks after administration; patients who receive these drugs require protection from light until the drug has been completely cleared from the skin. Other photosensitizers are activated in the vasculature; these drugs are activated within minutes of light delivery, and are cleared rapidly. This quick clearance allows the drug and light to be administered in the same treatment session, and avoids the need for prolonged light protection.

Embodiments include several modifications to the optical probe and associated equipment to facilitate PDT for TFT applications to treat tissue identified in a generated image as noted herein:

1. Addition of an LED at NIR range to fluorometer to deliver light to PCa;
2. Modifications to software to facilitate above 1; and
3. Modifications to probe with single or multiple sensors to deliver NIR light to PCa for therapeutic efficacy.

Brachytherapy (See FIG. 4 which Illustrates Brachytherapy in which Pellets have been Placed within the Prostate):

Brachytherapy (the term is derived from the Greek word brachys, which means brief or short) refers to cancer treatment with ionizing radiation delivered via radioactive material placed a short distance from, or within, the tumor. In PCa, brachytherapy involves the ultrasound- and template-guided insertion of radioactive seeds into the gland. Permanent seed brachytherapy, also known as low dose rate brachytherapy, involves having tiny radioactive seeds implanted in the prostate gland. Radiation from the seeds destroys cancer cells in the prostate over time. In addition to permanent brachytherapy, temporary brachytherapy has also been used. In this technique, the implants deliver radiation to the prostate at a higher dose rate than is provided by a permanent implant. Currently, the isotope most commonly used for temporary brachytherapy is iridium (Ir)-192, which provides a higher dose of radiation than the iodine (I)-125 and palladium (Pd)-103 permanent implants. Low dose rate prostate brachytherapy is an effective treatment for localized PCa. Recently, it has been considered for use in a focused manner whereby treatment is targeted only to areas of prostate cancer. The objective of focal brachytherapy for potential TFT applications is to provide effective cancer control for low-risk disease but with reduced genitourinary and rectal side-effects in a cost-effective way. Embodiments include modification to the technology to facilitate focal brachytherapy for TFT applications. At least two configurations can be incorporated to treat tissue identified in a generated image as noted herein:

1. Removable probe with a single sensor coupled with a cannula (outer needle). This is inserted via brachytherapy template until a PCa lesion is located. Sensor is then removed and a radioactive seed is inserted into the outer cannula. It is then pushed via metal tubing to the exact location where PCa lesion is located.
2. Probe with a seed-notch coupled with an outer needle. In this mechanism, radioactive seed is already hidden inside the notch covered by the outer needle. Once the sensor locate PCa lesion, trigger mechanism fires and leave the radioactive seed where PCa lesions is located.

HIFU:

Similar TFT applications may be achieved using high-intensity focused ultrasound (HIFU). HIFU is a treatment that uses ultrasound wave energy focused on the prostate via a transrectal probe to treat tissue identified in a generated image as noted herein. Multiple focal areas of destruction are created within the prostate. The prostate tissue is destroyed through coagulation by the ultrasound wave energy causing rapid heat elevation to about 90° C. at the focal point. An optical biopsy needle and/or an optical needle probe may be used separately or as an integrated device for HIFU treatment of PCa in TFT applications.

AC/DC Current for PCa Tissue Ablation:

Tumor efficacy is achieved by passing AC or DC current across PCa tissue by strategically placed electrodes to treat tissue identified in a generated image as noted herein. An optical probe can be used for identification of locations of PCa lesions and thereby enabling strategic placement of the electrodes. In an alternative configuration, both the electrode and optical sensor may be an integrated unit enabling concurrent diagnosis followed by ablation of each PCa lesion.

Laser Ablation:

Laser ablation could be yet another method to ablate the cancer tissue identified within the prostate once the locations of the cancer lesions are found in a generated image as noted herein. A variety of laser types have been developed for use in medical applications. These lasers may be routed to each PCa lesion using an optical needle probe with either single or multiple sensors.

RF Ablation:

RF ablation is yet another method to treat the identified cancerous tissue within the prostate gland to treat tissue identified in a generated image as noted herein. RF ablation is currently approved for treatment of BPH (benign prostate hyperplasia) and is commercially available.

Vapor Ablation:

Vapor ablation is a modality to treat cancer or other type of abnormal tissues within the body such as to treat tissue identified in a generated image as noted herein. Instead of using electrical, laser, or tissue freezing modalities, vapor with high temperature is used to shrink tissue or tumor.

Local Drug Delivery:

once the 3D mapping system has identified the location of cancerous tumor within the prostate, using the same or another needle, drugs and pharmaceutical agents could be delivered as means of treating the cancer locally.

3D Optical Imaging

Figure 6:
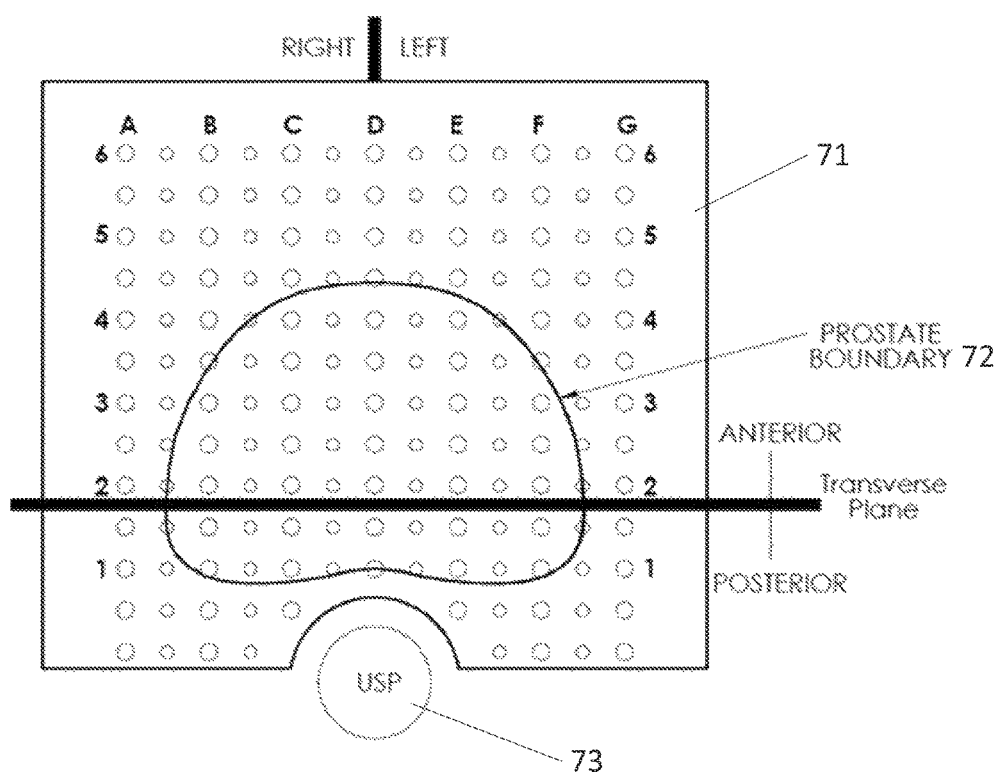
FIGS. 6 and 7 illustrate a coronal view of brachytherapy template and a prostate gland, and a sagittal view of the template, optical probe array including optical sensors, prostate gland, and USP according to embodiments.
Figure 7:
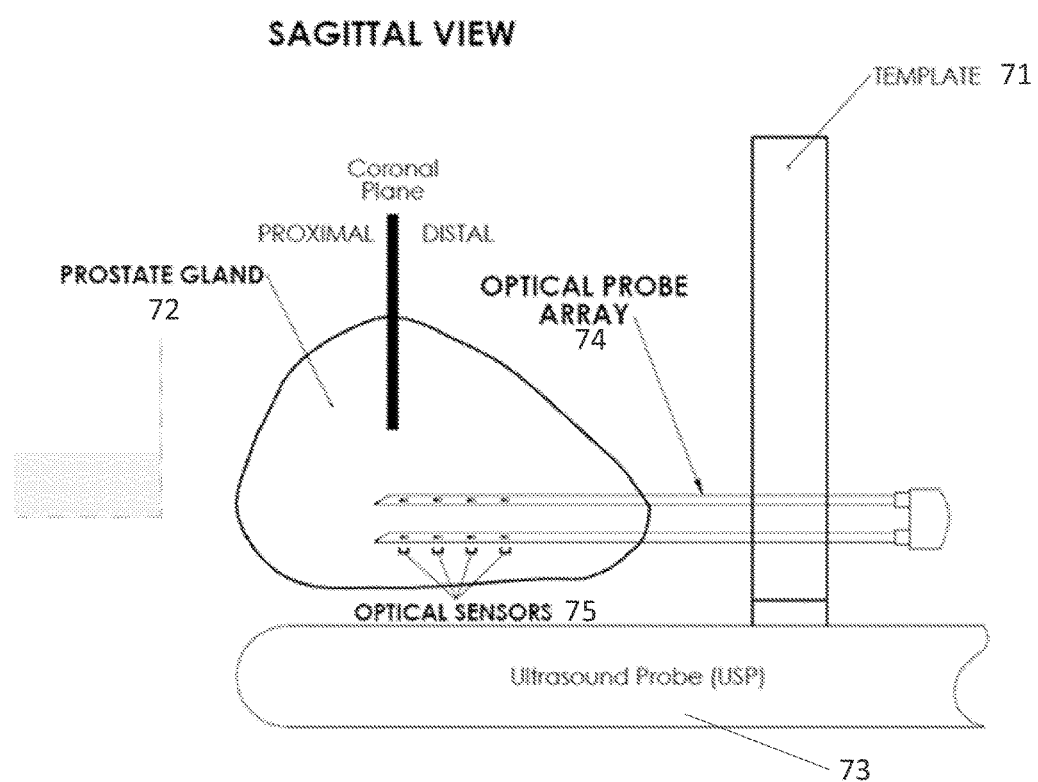

FIGS. 6-10 illustrate one embodiment of a system for use with a patient in the lithotomy position. FIG. 6 illustrates a coronal view of a brachytherapy template 71, a prostate gland 72, and an ultrasound probe (USP) 73. FIG. 7 illustrates a sagittal view of the template 71, an optical probe array 74 including optical sensors 75, the prostate gland 72, and the ultrasound probe 73 according to embodiments. In one embodiment, the template 71 may have alternating columns of openings of different diameter to accommodate different size probes, although any size opening and any type of hole configuration may be part of the template 71.

Figure 9:
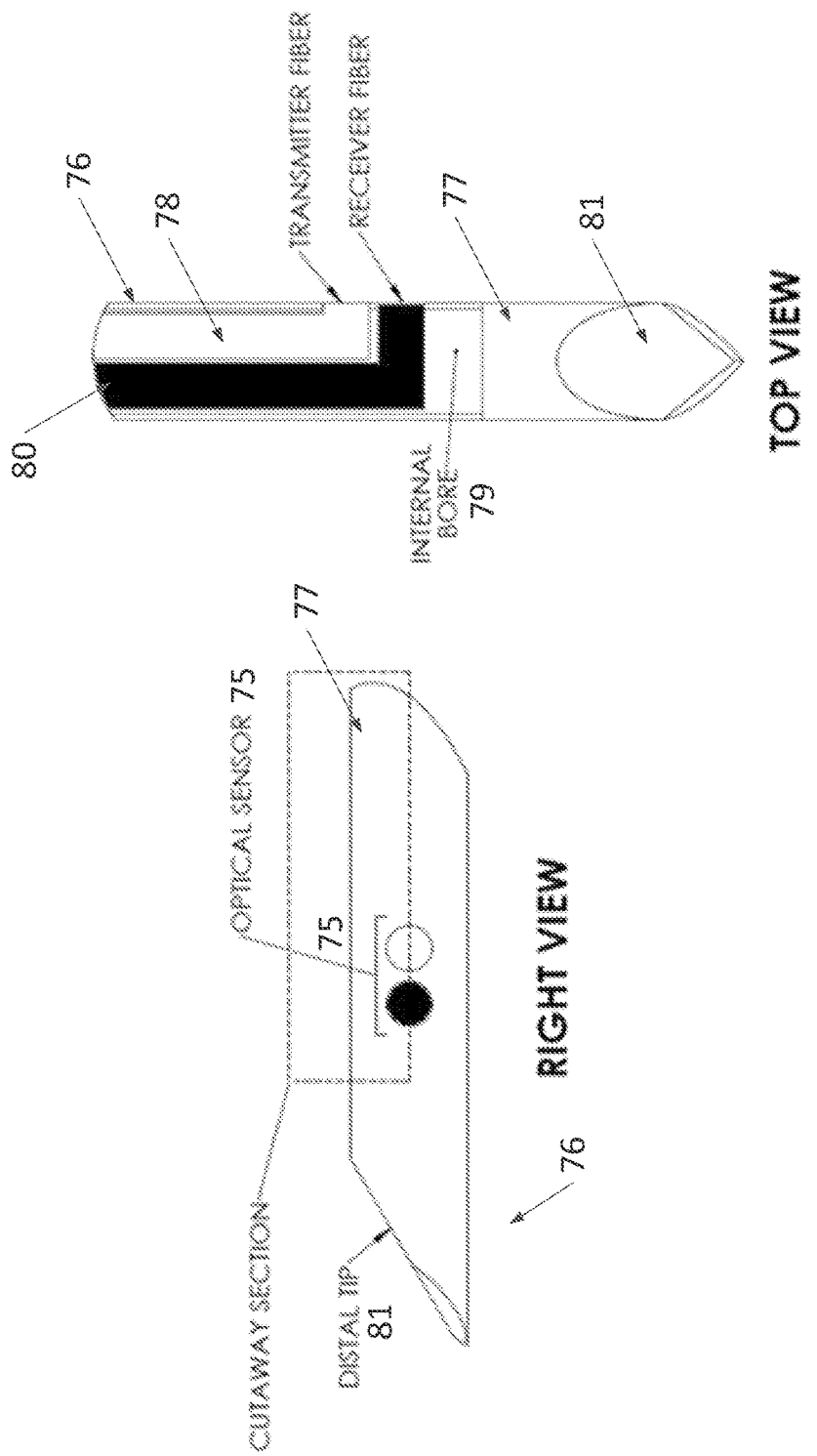
FIG. 9 illustrates a right side view and a top view with a portion cut away of a tip of a fiber optic probe according to one embodiment.

FIG. 8 illustrates tips of a 2×2 fiber optic probe array 74 with optical sensors 75 shown in a partial exploded view and the 2×2 fiber optic probe array 74 with optical sensors 75 in combination with a perineal 13×13 grid template 74 according to one embodiment. FIG. 9 illustrates a right side view and a top view with a portion cut away of a tip of a fiber optic probe 76 according to one embodiment. In one embodiment, the probe 76 comprises a hollow tube or shaft 77, a light source comprising a transmitting fiber optic 78 positioned within a bore 79 of the hollow tube 77 and supported by the shaft 77 to illuminate the tissue located near or at an end of the hollow tube or at angle with respect to the axis of the hollow tube, and a receiving optical fiber 80 positioned within the hollow tube to detect light from the illuminated tissue. In one form, the fiber 80 transmits the detected light to an optical light sensor which is part of an optical system (e.g., see FIG. 10 and optical system 115, below). Alternatively or in addition, light sensors may be positioned on the shaft 77. In one form, a distal tip 81 is tapered to facilitate insertion into the prostate gland.

Figure 10:
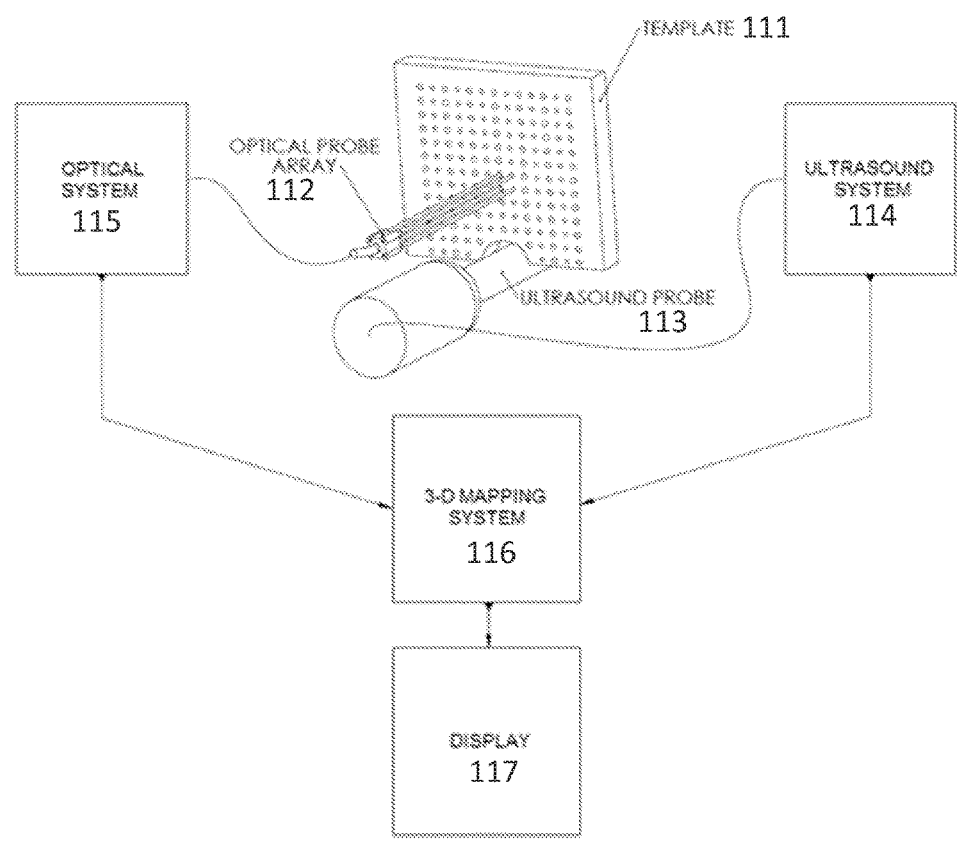
FIG. 10 illustrates a block diagram of an imaging system to diagnose and identify cancer lesions of the prostate according to one embodiment.

FIG. 10 illustrates a block diagram of a system for 3D imaging of the prostate according to one embodiment. The patient is positioned in the lithotomy position and a spatial template 111 or grid is placed against the perineum for aligning optical probes of an array 112 into a predetermined orientation relative to each other and relative to the tissue. The optical probe array 112 is guided into the prostate under imaging guidance (e.g. transrectal ultrasound probe 113 connected to an imaging guidance system 114) so that the optical sensors are within the prostate gland. Thus, the imaging guidance system 114 identifies the position of the optical probes of the array 112 relative to the prostate tissue. An optical system 115 which comprises at least one light source and at least one light detector (e.g. spectrometer) transmits to and receives light from the optical probe array 112. Light received by the optical system 115 is collected by the light sensor or detector, then digitized and processed (e.g., through a diagnostic algorithm) giving an indication of tissue condition (e.g. the presence or absence of disease). Diagnostic information from the optical system 114 is then combined with spatial information from the ultrasound probe 113 (e.g. probe and probe sensor positions within the prostate are stored). Once an acquisition has been performed, the probe array 112 can be moved to a new site within the prostate to perform additional acquisitions. With acquisitions covering sufficient volume of the prostate, a three-dimensional diagnostic imaging system 116 forms a 3D map of the imaged prostate gland based on the generated light signals and the identified position of the optical probe 112. The imaging system 116 and/or a 3D map displayed as an image on display 117 can be used to guide targeted therapeutic modalities to positions where lesions have been identified.

Among other things, the system includes an ultrasound transducer and sensor (e.g., probe 113) with ultrasound control system 114, an optical probe array 112 connected to an optical control system 115, a template 111 or other spatial control device (e.g. a grid), a 3-D imaging system 116 (e.g. a processor, memory user software, and graphical display) and an optional therapeutic modality system (e.g., a processor, not shown) for analyzing the test results. A fluorometer (not shown), spectrometer (not shown) or other optical phenomena detecting device with user interface software and tissue classification algorithm may be part of the optical system 115.

In one embodiment, the optical system 115 includes light sources such as LEDs, broadband tungsten-halogen or xenon lamps or lasers that transmit light to the tissue under examination through at least one optical fiber. Light reflected or emitted from the tissue under examination is routed via optical fiber or fibers to at least one optical detector or sensor of the optical system 115. The light sources and detectors are controlled by the optical system 115 which comprises a processor, memory, and communication components similar to a computer. The optical probes of the array 112 are positioned adjacent to or inserted into inside the prostate (or other tissue) through a transperineal grid template or other methods in order to create a 3-D image of the prostate based on tissue fluorescence and/or based on any other type of light spectroscopy measurements based on scattering phenomena of the tissue to reflect, shift (Raman scattering), absorb or scatter light or other energy (e.g., ultraviolet). In general, it has been found that the tissue is somewhat translucent and that when the tissue is illuminated with light energy, the energy tends to penetrate about 0.3 mm to 3.0 cm, depending on the wavelength and intensity. In addition, depending on wavelength and tissue composition, some tissue tends to fluoresce or otherwise provide excitations of varying wavelengths or other optical phenomena. Other energy may result in different penetration and response, depending on the type of tissue, its location and composition.

Using the spectroscopy measurements, tissue abnormalities are identified and mapped. For example, using fluorescence spectroscopy, NADH, tryptophan, and collagen components of the tissue will be identified as correlated to tissue abnormalities and mapped. Similarly, diffuse reflectance, scattering or absorptive light also provide irregularities and discontinuities in cell nuclei, cellular boundaries, etc., and presence/absence of various proteins as correlated to tissue abnormalities. This information can be translated for tissue classification for the purpose of identifying benign, malignant, calcified, and other components are labeled within the 3D optical mapping image.

Figure 11:
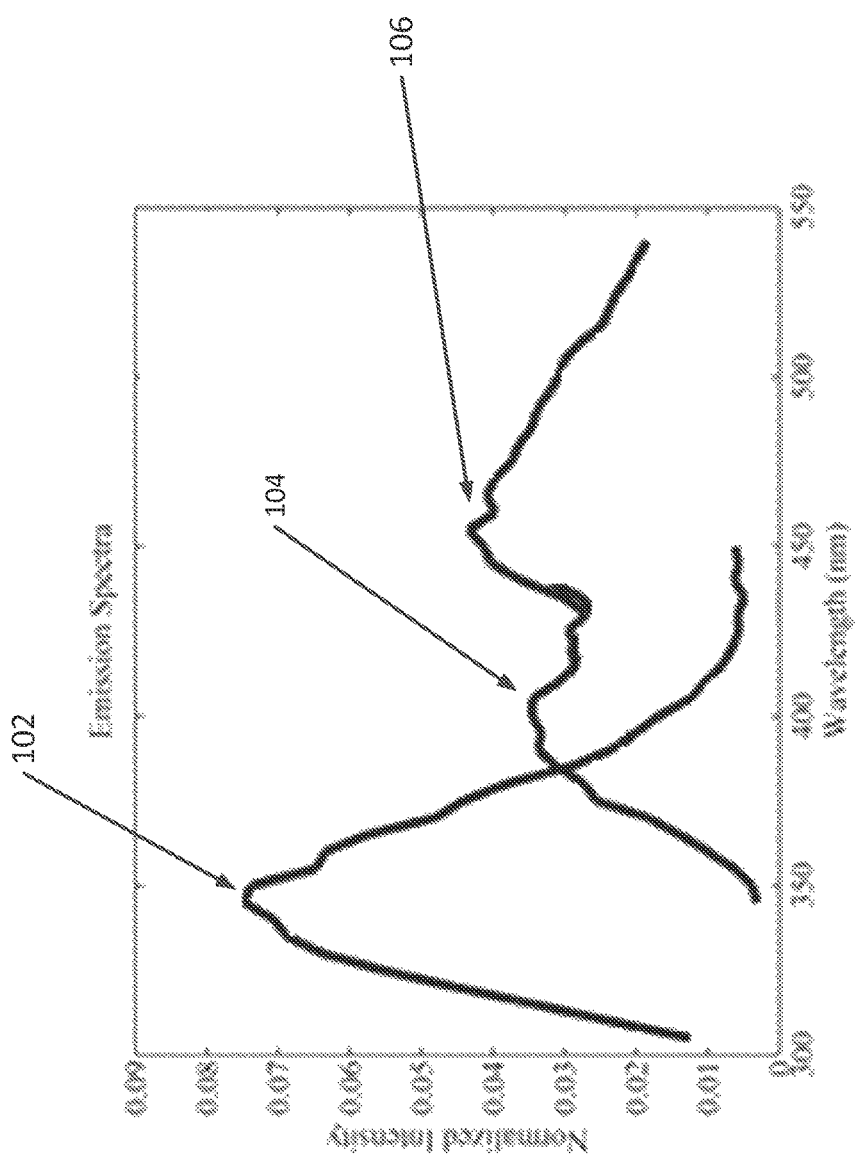
FIG. 11 illustrates the typical fluorescence spectra of prostate tissues for 290 and 340 nm excitation where peaks 102, 104 and 106 correspond to tryptophan, collagen, and NADH 104. X-axis represents emission spectra measured between 300 nm and 550 nm and Y-axis represents normalized intensity measured between 0.01 and 0.09.

There are a number of endogenous fluorophores available in human tissue (See Table 1, below). FIG. 11 illustrates the typical fluorescence spectra of prostate tissues for 290 and 340 nm excitation where peaks 102, 104 and 106 correspond to tryptophan, collagen, and NADH 104. X-axis represents emission spectra measured between 300 nm and 550 nm and Y-axis represents normalized intensity measured between 0.01 and 0.09. Collagen spectra can be obtained by excitation of tissue with a light source at 320-340 nm. NADH spectra can be obtained by excitation of tissue with a light source at 350-370 nm. As illustrated in FIG. 11, tryptophan spectra 102, collagen spectra 104, and NAHD spectra 106 register peak values at approximately 350 nm, 400 nm, and 460 nm, respectively.

Figure 12:
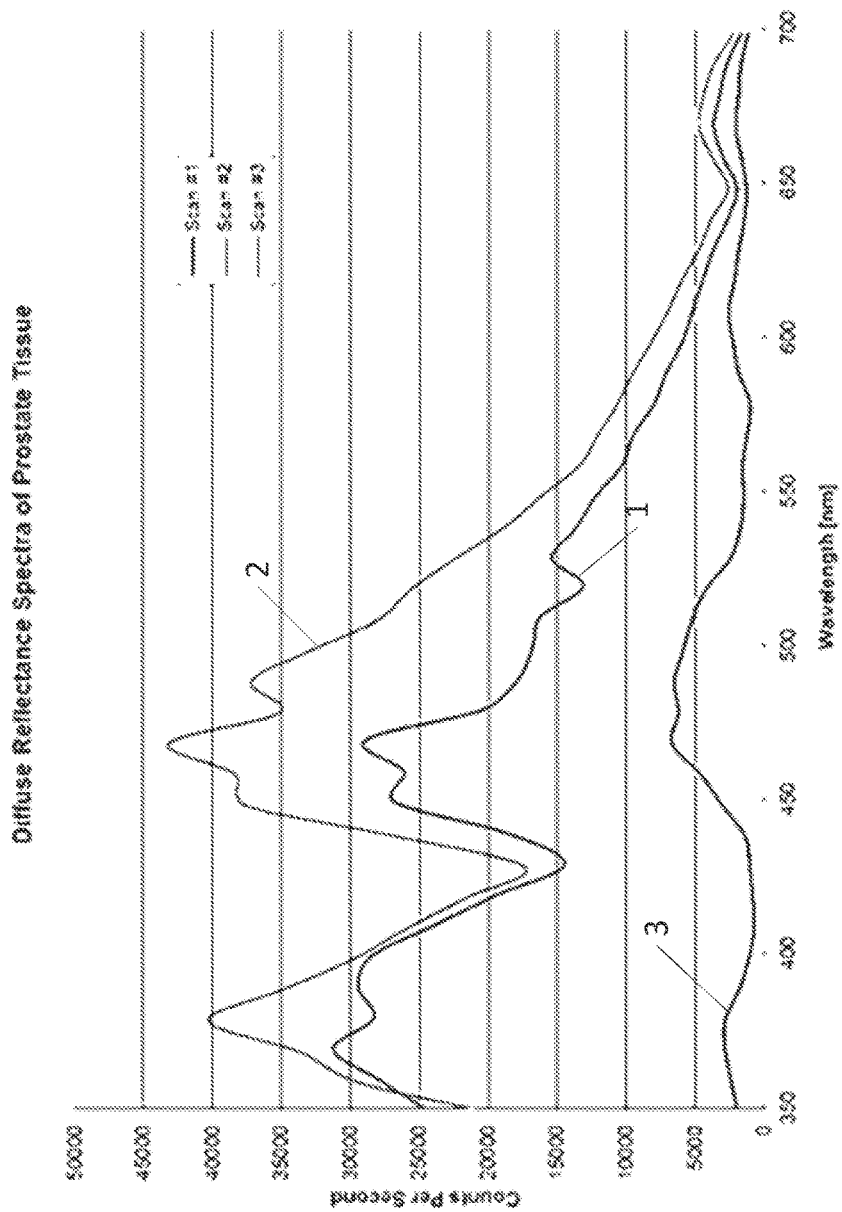
FIG. 12 illustrates typical diffuse reflectance spectra of prostate tissue. Each scan represents diffuse reflectance spectra obtained from different locations.

FIG. 12 illustrates typical diffuse reflectance spectra of prostate tissue for three different scans 1-3 taken by an optical probe array at three different locations within the prostate gland. Each scan represents diffuse reflectance spectra obtained from different locations. Diffuse reflectance spectra (DRS) provide architectural information about the tissue rather than chemical composition. Light photons scatter, bounce, and even get absorbed by the tissue. Diffuse reflectance spectroscopy, sometimes known as Elastic Scattering Spectroscopy, is a technique that measures the characteristic reflectance spectrum produced as light passed through a medium. The primary mechanisms are absorption and scattering, both of which vary with wavelength to produce the reflectance spectrum that is recorded. This spectrum contains information about the optical properties and structure of the medium being measured.

FIG. 12 illustrates typical DRS spectra of prostate tissue captured between 350 nm-700 nm inclusive of visible (VIS) range along the x-axis and intensity counts per second along the y-axis as a result of illuminating the tissue with a broadband light source having a wavelength range of at least 350 nm to 700 nm Counts on y-axis are the measure of intensity at each wavelength. The spectrum is measured between 350-700 nm range at 5 nm intervals. The range along the x-axis (independent variable) is chosen and the intensity on y-axis (dependent variable) is measured.

There are two absorption features approximately 425 nm and 650 nm and variation in the slope between 475 nm-650 nm. If a broader band light source is used to illuminate the tissue (e.g., 350 nm to 1200 nm), additional features may be available from 700 nm-1200 nm (not shown) inclusive of near infrared (NIR) as well. These features may be utilized for prostate tissue classification. DRS primarily probes morphological features and has proven to be sensitive to histological grades. Gleason grade, which characterizes aggressiveness of PCa lesions based on glandular architecture, is a valuable prognostic variable. Patients with PCa of Gleason grade 4 or 5 are known to have poor clinical prognosis. Since light is scattered at cells or intracellular structures, DRS data contains structural information of the medium. Hence, the structural information in DRS can be used to differentiate low grade (Gleason score=6) from high grade (Gleason score≥7) carcinoma as well as classify benign versus malignant tissue.

Figure 13:
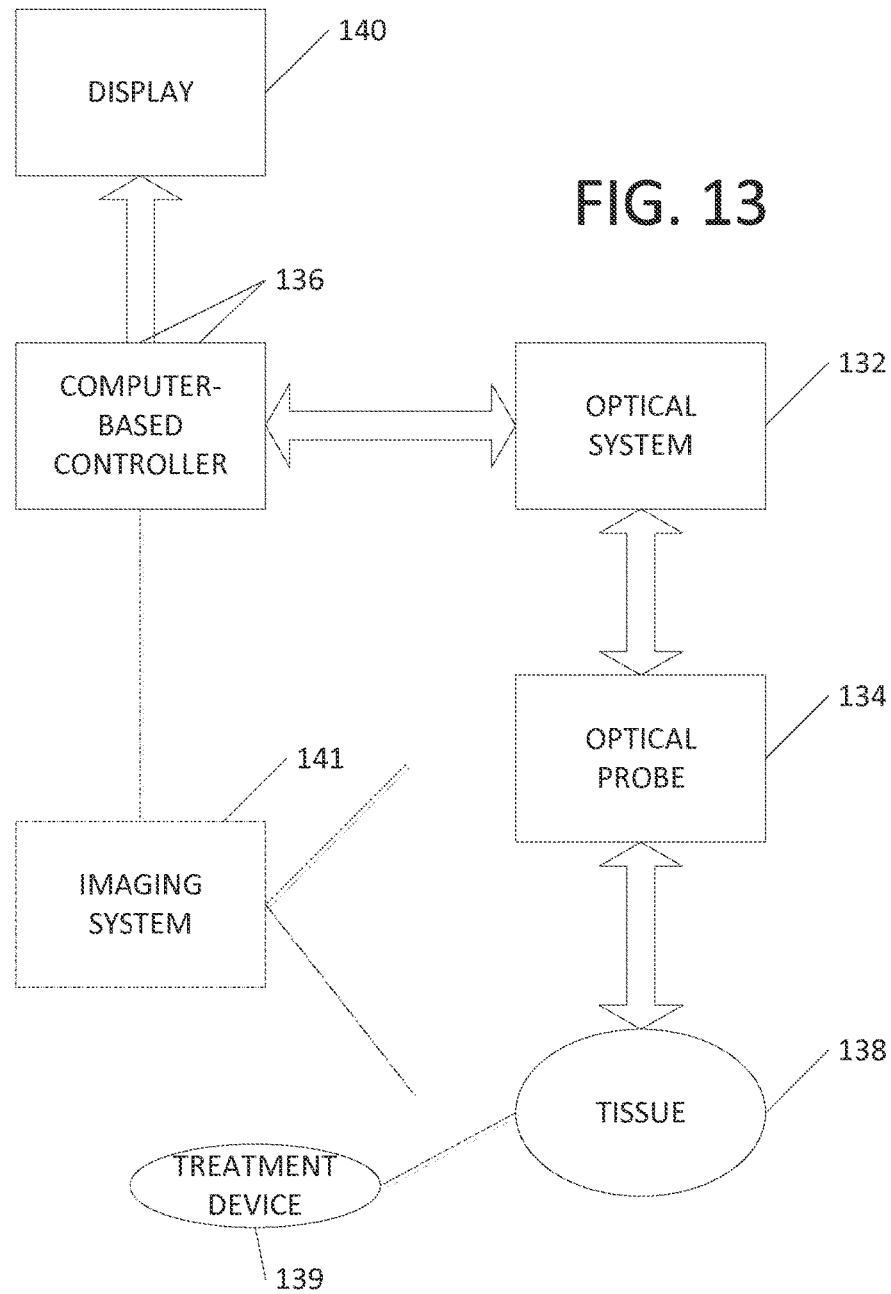
FIG. 13 illustrates in block diagram form one embodiment of an optical system connected to an optical probe and a computer controller executing user interface software and a tissue classification algorithm.

In one embodiment, a fluorometer has a connector where it can communicate with an ultrasound system used within prostate cancer diagnostics and therapeutic procedures. User interface software is used to capture 3D transrectal ultrasound (TRUS) images of the prostate. Grid coordinates of brachytherapy template will be superimposed on 3D TRUS image of the prostate. Software enables users to highlight each XY coordinate position as well as Z coordinate (depth of the prostate) when cancer is identified. An optical probe is inserted into each grid coordinate point and fluorescence spectra are captured using the fluorometer. FIG. 13 illustrates in block diagram form one embodiment of an optical system 132 such as a fluorometer connected to an optical probe 134 and connected to a computer-based controller 136 executing user interface software and a tissue classification algorithm. The fluorometer 132 transmits light from a light source or sources through the probe 134 where light interacts with the tissue 138 and is received and transmitted back to a detector inside the fluorometer 132. The fluorometer 132 is operated by the computer-based controller 136 which processes received signals and delivers via display 140 diagnostic classification of the tissue under examination to the user. Thus, the display 140 presents a graphical user interface which, in its simplest form, is a two or three-dimensional image of the tissue. Alternatively, the interface may provide the user with options so that the user can select various images or perspectives of an image. For example, the interface can give the user the option to select a two-dimensional image, a three-dimensional image, a fused image, or some other image variation. The interface can also provide the user with the option to select a black-and-white image, a color image, a line image or other image parameter variations. Optionally, the system of FIG. 13 can be used in combination with an imaging system 141 such as an ultrasound system or a MRI/CT system or both for identifying the position of the optical probes relative to the tissue. (See also FIG. 23). A treatment device 139 employing a treatment modality such as described herein can be used in combination with the imaged or mapped tissue to treat the imaged tissue. For example, the device 139 can be a Cryotherapy device; a Photodynamic Therapy device; a Brachytherapy device; a high-intensity focused ultrasound (HIFU) device; a tissue ablation device; a Laser ablation device; a RF ablation device; a Vapor ablation device; and a Local drug delivery device.

In one embodiment, when the tissue classification algorithm indicates that the location is positive for cancer based on fluorophores tryptophan, collagen, and NADH, an operator estimates the location (e.g., the depth of insertion on live TRUS image of the prostate) and highlights corresponding XYZ coordinates in the 3D TRUS image on the fluorometer. The above process continues until all grid coordinates overlapping the prostate are complete. Each optical sensor measurement will be correlated to an ultrasound coordinate so that the optical sensor measurements and the ultrasound image can be overlapped to create the 3D optical image of the prostate. This is shown in the FIG. 5A which illustrates a 3D optically mapped image of the prostate following optical measurements identifying locations of prostate cancer lesions according to one embodiment. FIG. 5A shows a 3D cross section of XYZ coordinates and FIG. 5A shows tumor volume estimates based on optical sensor readings. At the completion of optical measurements and tissue classification using the algorithm, a 3D image of the prostate based on the optical measurements is generated. Optionally, image analysis software can be used to analyze the image of FIG. 5A to generate a corresponding line drawings as shown in FIG. 5B.

Endogenous fluorophores in biological tissues include FAD, NADH, collagen, elastin, tryptophan, tyrosine, phenylalanine, some vitamins, and lipids (which are main components of the cell membrane and some organelles). Excitation light at 290 and 340 nm is currently being used to classify prostate cancer tissue limiting us to items which excite near those wavelengths (see Table 1, below). However, additional excitation light sources may be added to excite other types of fluorophores to diagnose various other types of cancer based on further research. See table 1 below for an exemplary listing of endogenous fluorophores which may make up the components of tissue to be evaluation and their excitation maxima and emission maxima.

TABLE 1

| Endogenous fluorophores | Excitation minima (nm) | Emission maxima (nm) |
|---|---|---|
| Amino Acids | | |
| Tryptophan | 280 | 350 |
| Tyrosine | 275 | 300 |
| Phenylalanine | 260 | 280 |
| Structural proteins | | |
| Collagen | 325 | 400, 405 |
| Elastin | 290, 325 | 340, 400 |
| Enzymes and coenzymes | | |
| FAD, flavins | 450 | 535 |
| NADH | 290, 351 | 440, 460 |
| NADPH | 336 | 464 |
| Vitamins | | |
| Vitamin A | 327 | 510 |
| Vitamin K | 335 | 480 |
| Vitamin D | 390 | 480 |
| Vitamin $B_6$ compounds | | |
| Pyridoxine | 332, 340 | 400 |
| Pyridoxamone | 335 | 400 |
| Pyridoxal | 330 | 385 |
| Pyridoxic acid | 315 | 425 |
| Pyridoxal 5'-phosphate | 330 | 400 |
| Vitamin $B_{12}$ | 275 | 305 |
| Lipids | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

Data processing and a typical tissue classification algorithm are based on a support vector machine (SVM) or other statistical methods and systems suitable for classification such as linear discriminant analysis (LDA), artificial neural networks (ANN), multiple logistic regression, etc. Here we describe the procedure for SVM-based tissue classification, although it can be extended to other methods and systems as well. In machine learning, support vector machines (SVMs) are supervised learning models with associated learning algorithms that analyze data and recognize patterns, used for classification and regression analysis. The basic SVM takes a set of input data and predicts, for each given input, which of two possible classes forms the output, making it a non-probabilistic binary linear classifier. Given a set of training examples, each marked as belonging to one of two categories, an SVM training algorithm builds a model that assigns new examples into one category or the other. An SVM model is a representation of the examples as points in space, mapped so that the examples of the separate categories are divided by a clear gap that is as wide as possible. New examples are then mapped into that same space and predicted to belong to a category based on which side of the gap they fall on. In addition to performing linear classification, SVMs can efficiently perform non-linear classification using what is called the kernel trick, implicitly imaging their inputs into high-dimensional feature spaces.

Below is one example of a software data process of computer executable instructions stored on a tangible, non-transitory storage medium and executed by a processor to validate data based on a support vector machine (SVM):

Raw Data such as fluorescence spectra and histopathology of the tissue score is captured;

Conditioning of the raw data includes background subtraction and S/N ratio cutoff;

Preprocessing of the conditioned data involved data smoothing, interpolation and normalization;

Prostate Cancer evaluation includes partial least square (PLS) analysis of the preprocessed data;

Prostate Cancer selection involves statistical analysis of the evaluated data including reducing false positives (FP) and reducing false negatives (FN);

An algorithm executed on the selected data by a support vector machine (SVM) analyzes the selected data to provide a binary classification (cancer/no cancer) of the tissue under evaluation.

Validation of the analyzed data includes statistical analysis by such techniques as "leave one out" cross-validation and/or external analysis.

Figure 14:
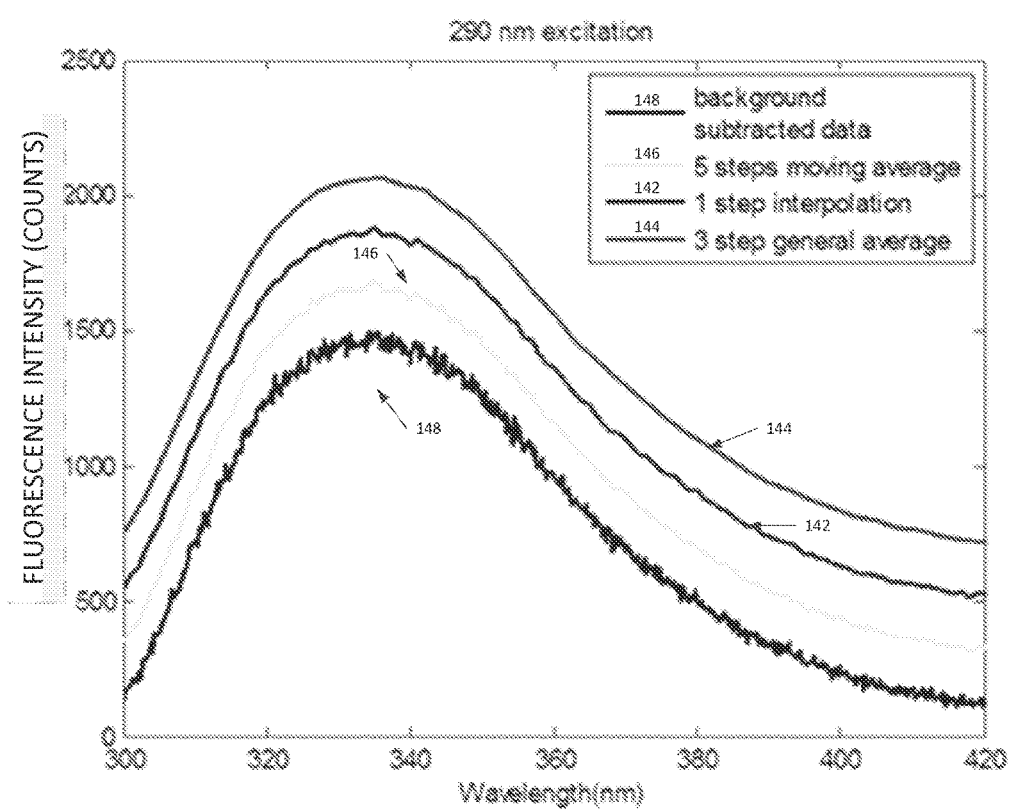
FIGS. 14-15 illustrate fluorescence intensity spectra of prostate tissue at 290 and 340 nm excitation being processed for analysis and classification, with fluorescence intensity (counts) along the y-axis and wavelength (nm) along the x-axis.
Figure 15:
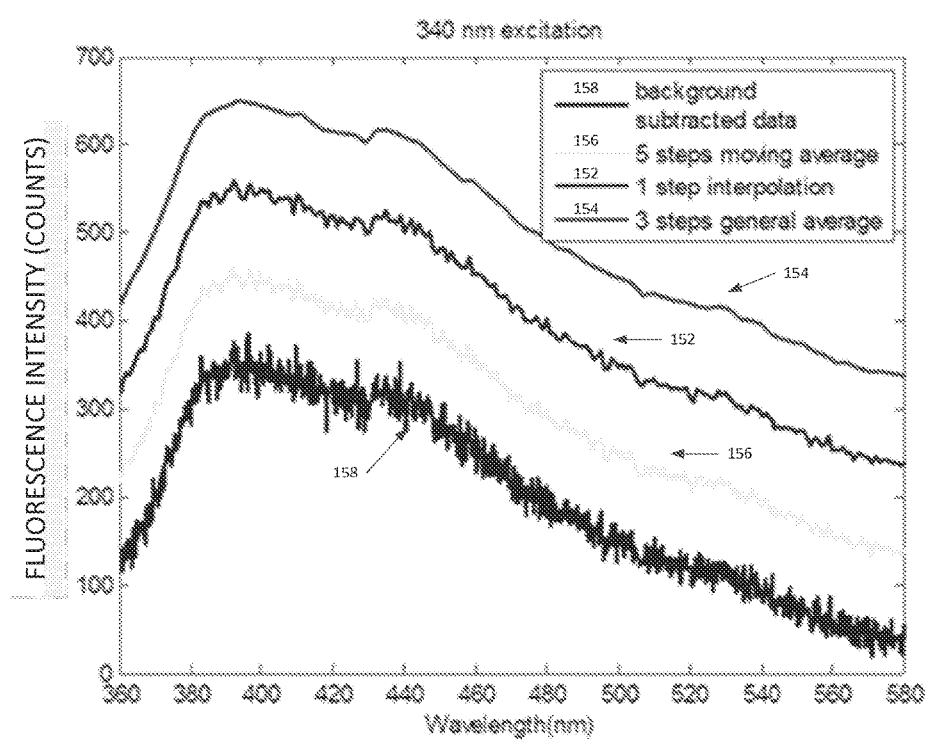
Figure 16:
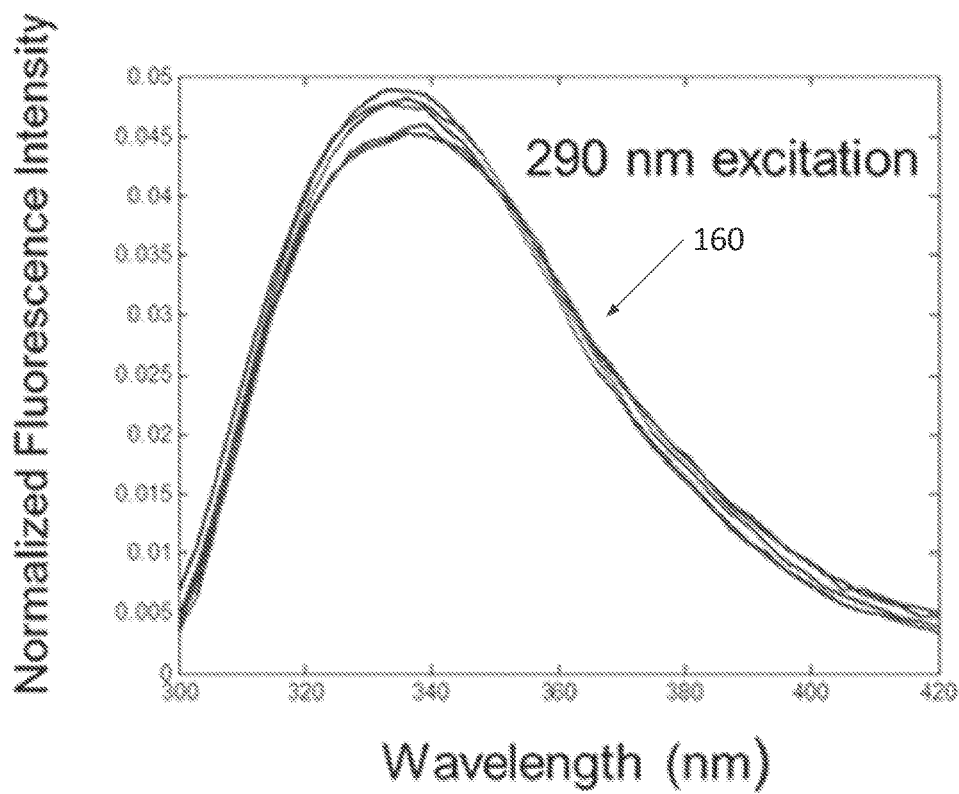
FIGS. 16-17 illustrate normalized fluorescence intensity spectra of prostate tissue at 290 and 340 nm excitation being processed for analysis and classification, with normalized fluorescence intensity along the y-axis and wavelength in nanometers (nm) along the x-axis.
Figure 17:
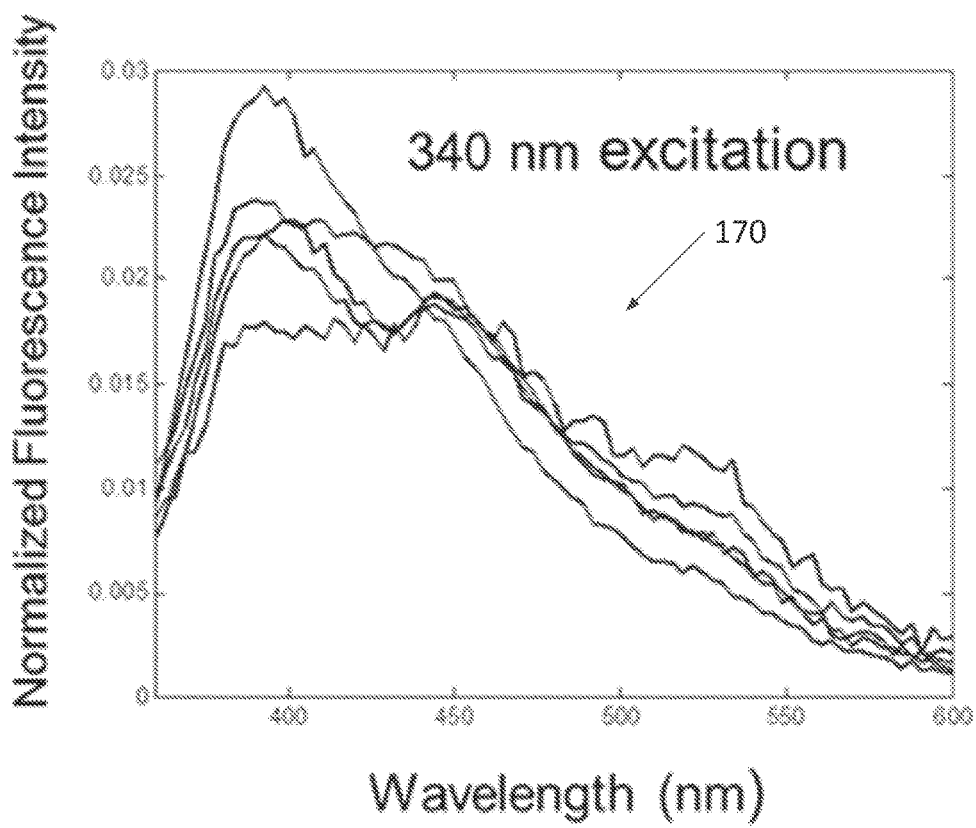
Figure 18:
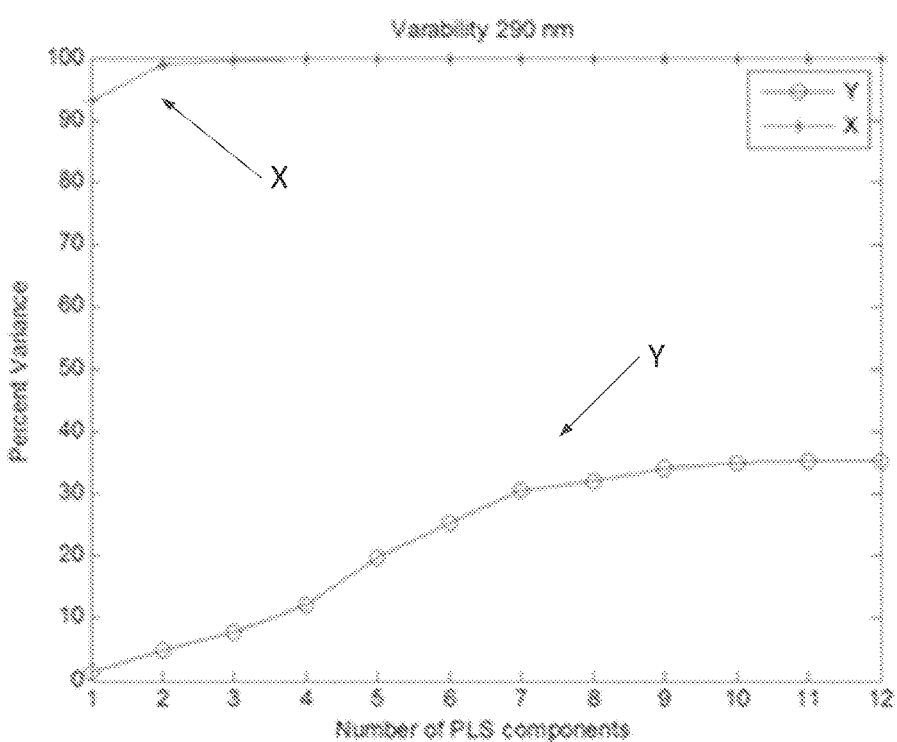
FIGS. 18-19 illustrate percentage variability in fluorescence spectra labeled X and histopathology data labeled Y associated with partial least square (PLS) components at 290 nm and 340 nm variability, with percent variance along the y-axis and number of partial least square (PLS) components along the x-axis.
Figure 19:
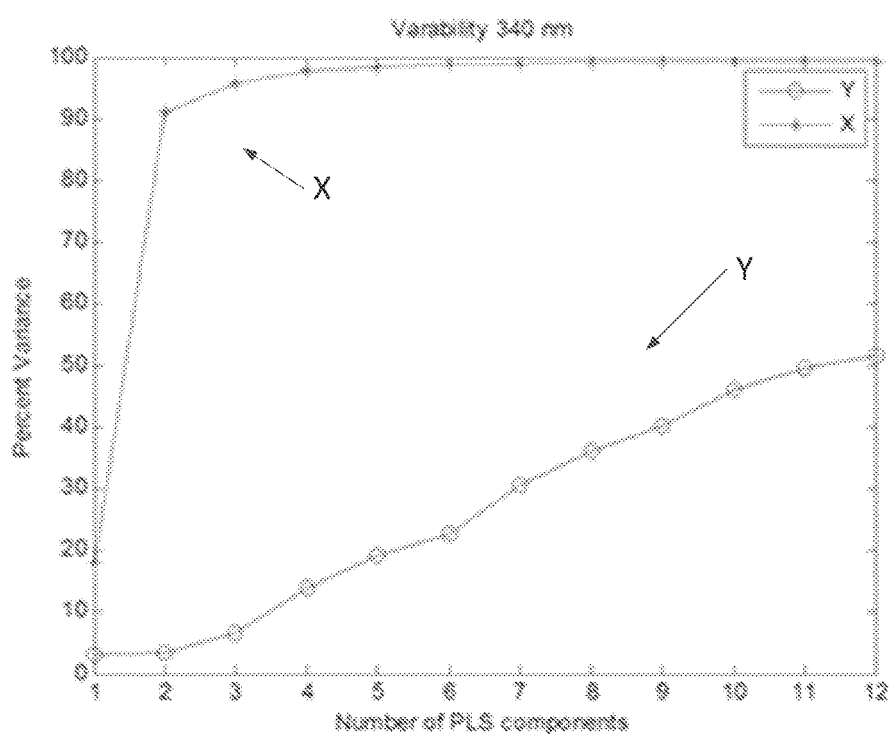

FIG. 14 illustrates fluorescence intensity spectra at 290 nm being processed for analysis and classification by 1-step interpolation 142, 3-step general average 144, 5-step moving average 146, and background data 148 which is subtracted. FIG. 15 illustrates fluorescence intensity spectra at 340 nm being processed for analysis and classification by 1-step interpolation 152, 3-step general average 154, 5-step moving average 156, and background data 158 which is subtracted. FIG. 16 illustrates several normalized fluorescence intensity spectra 160 at 290 nm excitation being processed for analysis and classification. FIG. 17 illustrates several normalized fluorescence intensity spectra 170 at 340 nm excitation being processed for analysis and classification. FIGS. 18-19 illustrate percentage variability in fluorescence spectra X and histopathology data Y associated with 1 to 12 PLS components at 290 nm and 340 nm variability, respectively.

In one embodiment, not all components in fluorescence spectra will have the same "weights." The partial least squares (PLS) analysis identifies which portions of the emission spectra are likely to contain unique features to help with determining the classification. PLS analysis will create a linear combination of weighted values relative to the size of the spectral data values. As an example, if there are 1000 discrete intensity values from a single emission spectra, there will be a weight matrix of the same number of discrete values (in this example, 1000 in all). An algorithm can be configured to focus on the interested component, say 12 partial least squares components, which in this example would create a matrix of size 1000 by 12 where each column vector represents the linear combination of weighted values for the single PLS analysis. FIG. 18 illustrates percentage variability in fluorescence spectra and histopathology data associated with 1 to 12 PLS components. A ranking test such as a Wilcoxon Rank Sum test is then used to determine which weight vectors are least significantly correlated since some features may be redundant due to tracking the identical fluorophores. Since PLS components for fluorescence spectra at different excitations may be correlated, Pearson correlation coefficient is tested to identify such correlations. In the event two PLS components are correlated, only one is selected for tissue classification. PLS will inherently create disproportionate weighting of spectral data in attempts of highlighting important features and suppressing less important elements. A feasibility study was conducted during July-December, 2012 to determine the efficacy of an optical biopsy needle adjunct with fluorescence spectroscopy for diagnosis of prostate cancer. A total of 208 in vivo biopsies (29 malignant) and 224 ex vivo biopsies (51 malignant) were studied. The next two tables summarize the SVM results for sensitivity (SE), specificity (SP), positive predictive value (PPV), negative predictive value (NPV), true positives (TP), true negative (TN), false positives (FP), and false negatives (FN) based on selected PLS components.

The following Tables 2 and 3 illustrate results as noted above:

TABLE 2

SVM Classification of Benign versus Malignant Disease For In Vivo Data

|  | PLSC#1-5 | PLSC#1-7 | PLSC#1-10 |
| --- | --- | --- | --- |
| TP | 17 | 21 | 19 |
| TN | 118 | 133 | 133 |
| FP | 29 | 14 | 14 |
| FN | 8 | 4 | 6 |
| SP | 80% | 90% | 90% |
| SE | 68% | 84% | 76% |
| PPV | 37% | 60% | 58% |
| NPV | 94% | 97% | 96% |

TABLE 3

SVM Classification of Benign versus Malignant Disease For Ex Vivo Data

|  | PLSC#1-5 | PLSC#1-7 | PLSC#1-10 |
| --- | --- | --- | --- |
| TP | 28 | 26 | 25 |
| TN | 132 | 136 | 138 |
| FP | 11 | 7 | 5 |
| FN | 4 | 6 | 7 |
| SP | 92% | 95% | 97% |
| SE | 88% | 81% | 78% |
| PPV | 72% | 79% | 83% |
| NPV | 97% | 96% | 95% |

Figure 20:
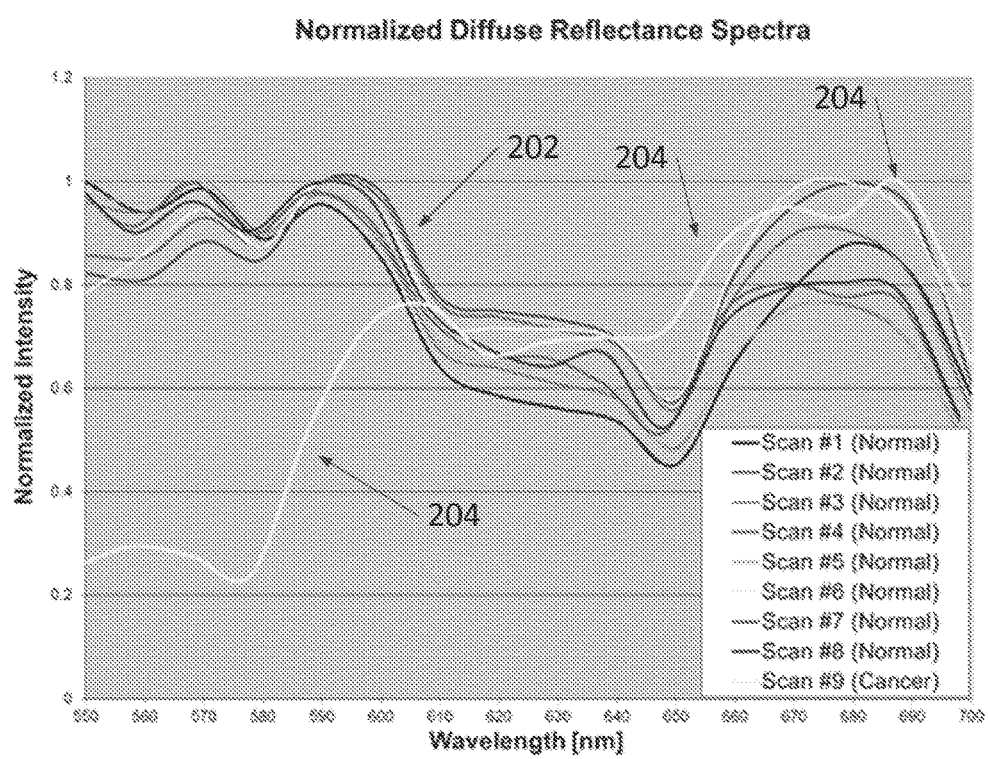
FIG. 20 shows typical normalized diffuse reflectance spectra scans of prostate tissue within the range of 550 nm-700 nm, with normalized intensity along the y-axis and wavelength (nm) along the x-axis.
Figure 21:
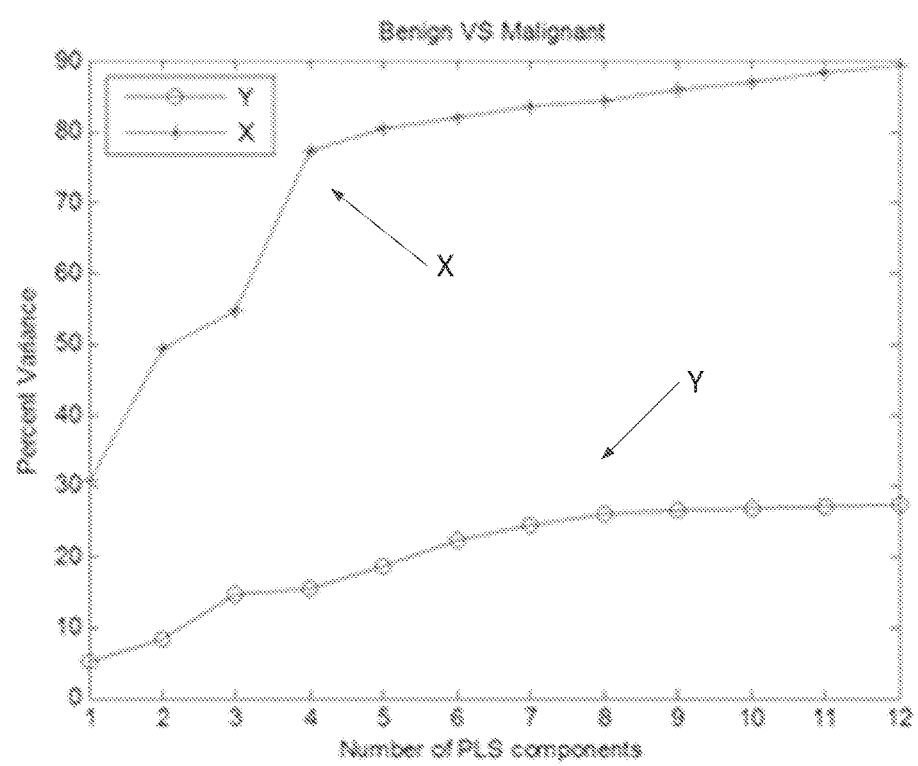
FIGS. 21-22 illustrate the percentage variability in diffuse reflectance spectra labeled X and histopathology data labeled Y associated with 1 to 12 PLS components for benign versus malignant and high grade versus low grade prostate tissue classification, respectively, with percent variance along the y-axis and number of PLS components along the x-axis.
Figure 22:
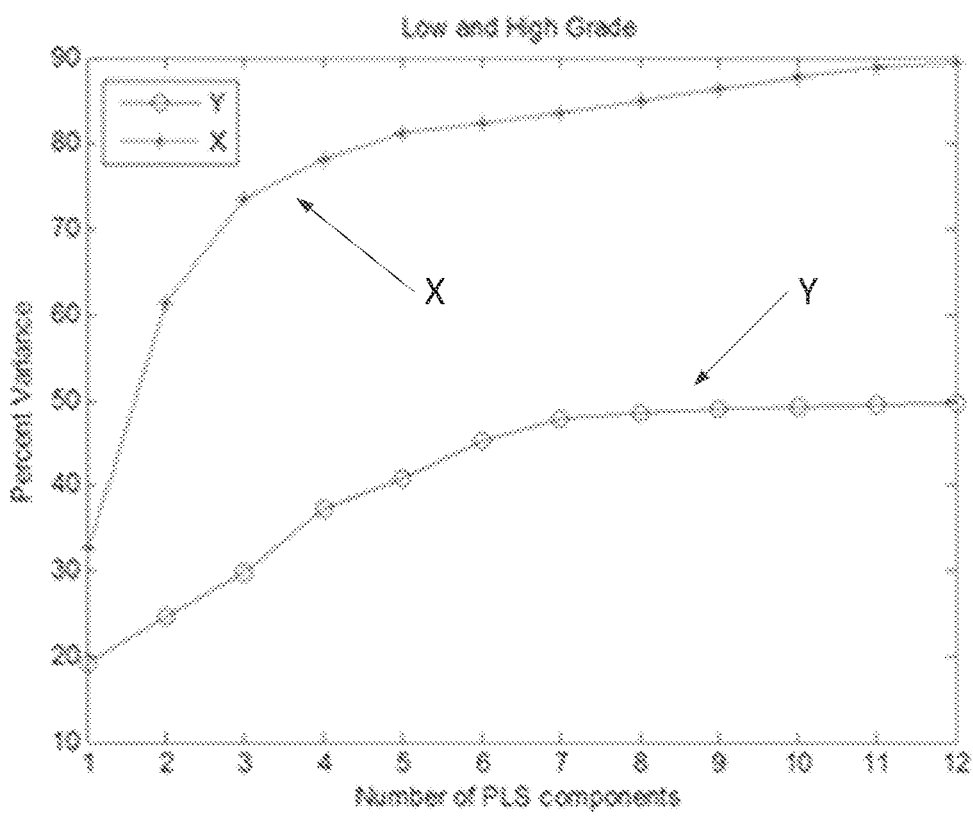

In one embodiment, diffuse reflectance spectra are processed as an adjunct to identify benign versus malignant disease as well as high (Gleason sum≥7) versus low (Gleason sum≤6) disease located up to 1 cm from the optical sensor. FIG. 20 shows typical normalized diffuse reflectance spectra scans for prostate tissue within the range of 550 nm-700 nm for eight (8) normal scans 202 and one cancer indicative scan 204. Histopathology of the biopsy core up to 1 cm length is taken into consideration for DRS. A total of 263 biopsy cores were analyzed Histopathological analysis classified 151 biopsy cores as benign and 112 as malignant. Out of 112 malignant cores, 61 were classified as low grade disease (Gleason score≤6) and remaining 51 were classified as high grade disease (Gleason score≥7). DRS data were processed according to steps outlined above based on a support vector machine (SVM). PLS components were computed and selected as previously described FIGS. 21-22 illustrate the percentage variability in DRS and histopathology data associated with 1 to 12 PLS components for benign versus malignant and high grade versus low grade prostate tissue classification, respectively. The percent variance is illustrated along the y-axis and the number of PLS components is illustrated along the x-axis. FIG. 21 illustrates percentage variability in spectral data X and histopathology Y associated with each PLS component. PLS attempts to minimize least square error while projecting X and Y data. By selecting a combination of PLS components, one can identify a minimum set of classifiers that best describe X and Y while keeping the percentage variability to acceptable levels. In this FIG. 21, PLS components #1-6 describes 80% out of 90% total variability of X and 25% out of 30% of total variability of Y. Therefore, PLS components #1-6 may be used in SVM for benign versus malignant tissue classification.

Similarly, FIG. 22 illustrates variability in spectral data X and histopathology Y associated with each PLS component. In this FIG. 22, PLS components #1-7 describes 85% out of 90% total variability of X and 48% out of 50% of total variability of Y. Therefore, PLS components #1-7 may be used in SVM for low versus high grade cancer tissue classification.

The following Table 4 summarizes typical values for sensitivity (SE), specificity (SP), positive predictive value (PPV), negative predictive value (NPV), true positives (TP), true negative (TN), false positives (FP), and false negatives (FN) obtained for this type of data set.

TABLE 4

Prostate Tissue Classification based on Diffuse Reflectance Spectra

| Classification | TP | TN | FP | FN | SE | SP | PPV | NPV |
| --- | --- | --- | --- | --- | --- | --- | --- | --- |
| Benign vs. Malignant | 73 | 105 | 57 | 39 | 65% | 70% | 61% | 73% |
| Benign vs. Low Grade | 44 | 106 | 45 | 17 | 72% | 70% | 49% | 86% |
| Benign vs. High Grade | 39 | 119 | 32 | 12 | 76% | 79% | 55% | 91% |
| High vs. Low Grade | 41 | 49 | 12 | 10 | 80% | 80% | 77% | 83% |

Figure 23:
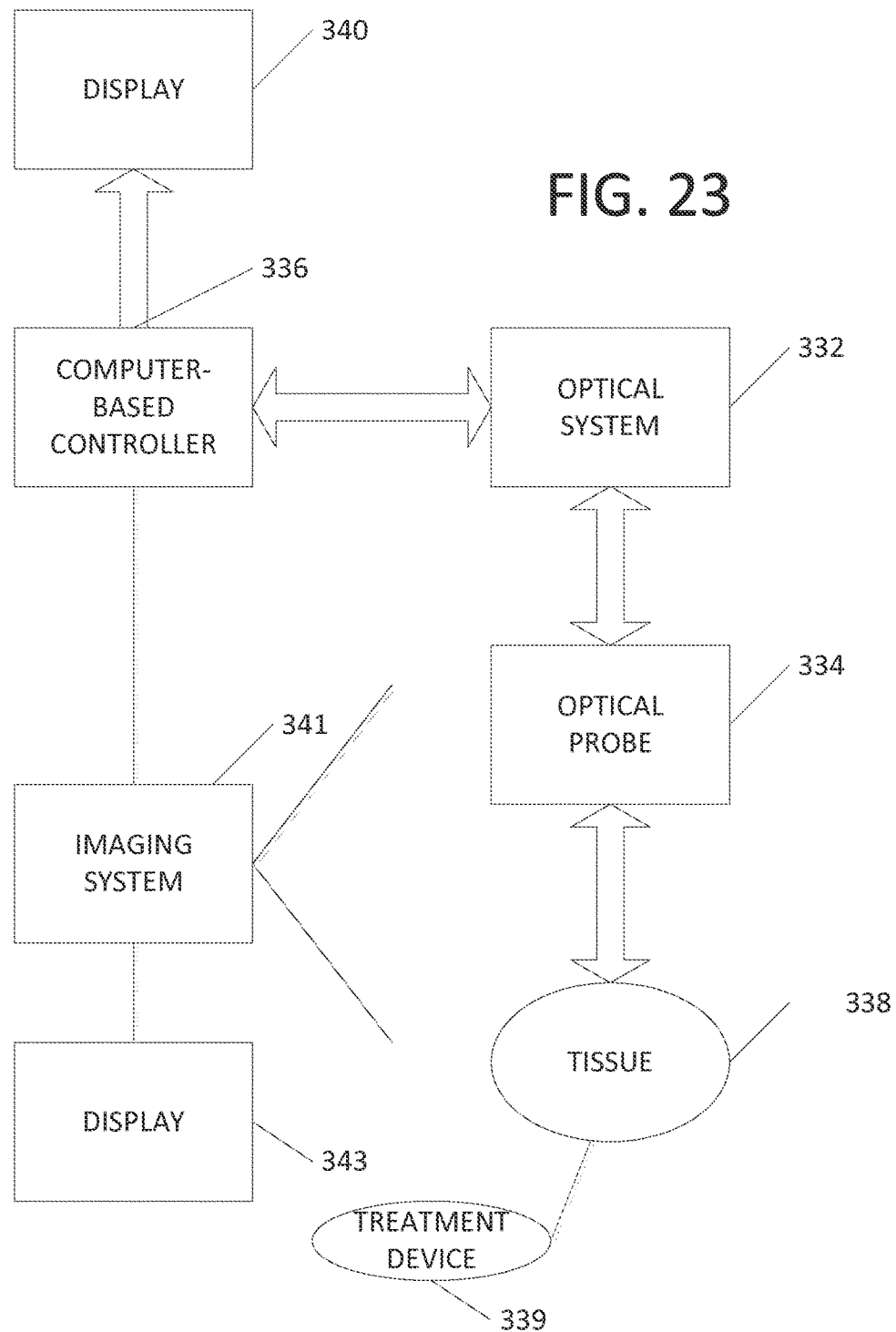
FIG. 23 illustrates in block diagram form one embodiment of an optical system connected to an optical probe and a computer controller executing user interface software and a tissue classification algorithm, in combination with an imaging system.

FIG. 23 illustrates in block diagram form one embodiment of an optical system 332 such as a fluorometer or a diffuse reflectance spectometer connected to an optical probe 334 and connected to a computer-based controller 336 executing user interface software and a tissue classification algorithm. The optical system 332 transmits light from a light source or sources through the probe 334 where light interacts with the tissue 338 and is received and transmitted back to a detector inside the optical system 332. The optical system 332 is operated by the computer-based controller 336 which processes received signals and delivers via display 340 diagnostic classification of the tissue under examination to the user. For example, the display 340 may be an image as illustrated in FIG. 11, 12 or 14-22. Thus, the display 340 presents a graphical user interface which, in its simplest form, is a two (or three) dimensional image indicate of the condition of the tissue as indicated by the light signal detected by the optical system 332. For example, the light signals are indicative of the light emitted, reflected and/or absorbed by the tissue. In addition, an imaging system 341 such as an ultrasound system or a MRI/CT system or both in combination has a display 343 which provides a fused US/MRI or US/CT image for identifying the position of the optical probe 334 relative to the tissue 338. Alternatively or in addition, the user interface on display 340 can provide the user with options so that the user can select various images or perspectives of an image. For example, the interface can give the user the option to select a two-dimensional image, a three-dimensional image, a fused image, or some other image variation. The interface can also provide the user with the option to select a black-and-white image, a color image, a line image or other image parameter variations.

Figure 24:
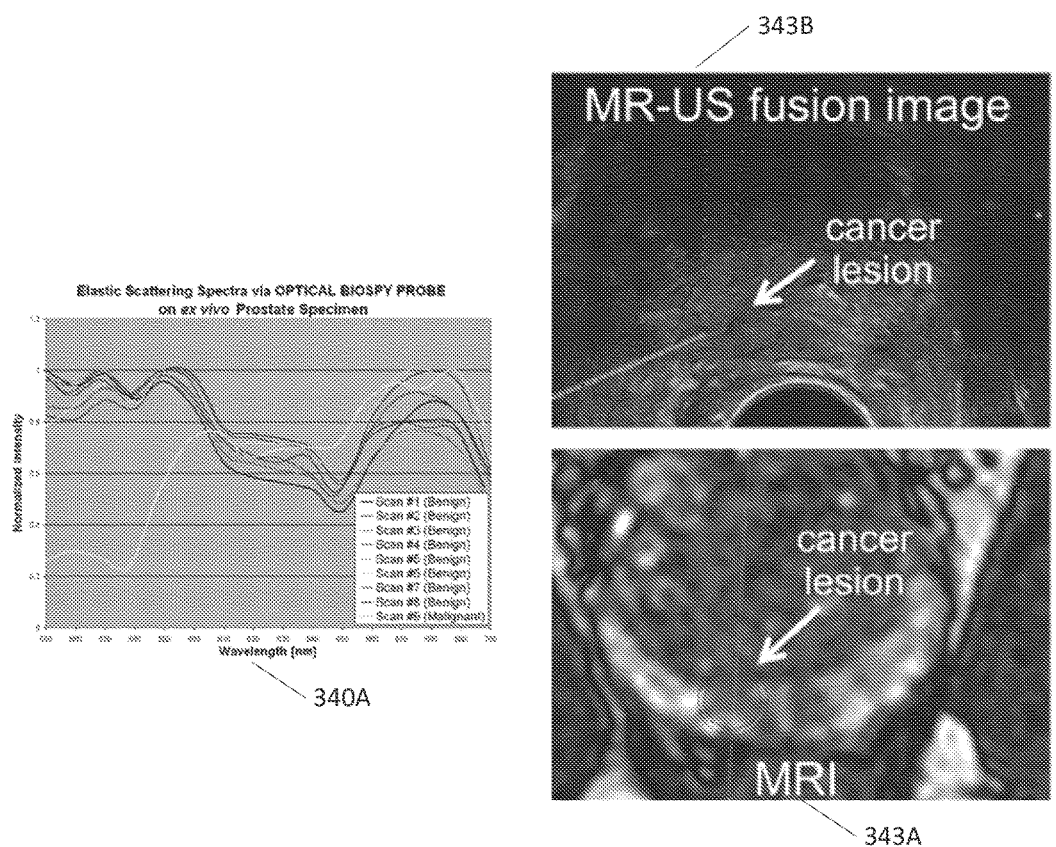
FIG. 24 illustrates two photographs on the right side, the bottom right photo is an MRI image where a cancer lesion was first diagnosed by a radiologist and the upper right photo is a MRI fusion image showing a cancer lesion fused with an ultrasound (US) image.

It is also contemplated that any of the above noted images may be combined or fused with a MRI image or CT image of the same tissue to provide additional diagnostic and treatment information. For example, FIG. 24 illustrates two photographs on the right side, the bottom right photo 343A is an MRI image where a cancer lesion was first diagnosed by a radiologist and the upper right photo 343B is a MRI fusion image showing a cancer lesion fused with an ultrasound (US) image. This combined MRI/US image can be used for transrectal or transperineal directed biopsy of the prostate. When an optical biopsy needle 334 is used, elastic scattering spectra (e.g., FIG. 12) can be generated in the computer monitor display 340 from the location or vicinity of the cancer lesion shown in MRI/US fusion image. FIG. 24 illustrates one photograph 340A on the left side which illustrates elastic scattering spectra. This elastic scattering spectra presented on display 340 when processed by a tissue classification algorithm, can either confirm or contradict the existence of a cancer lesion shown in MRI/US fusion image 343B.

Figure 25:
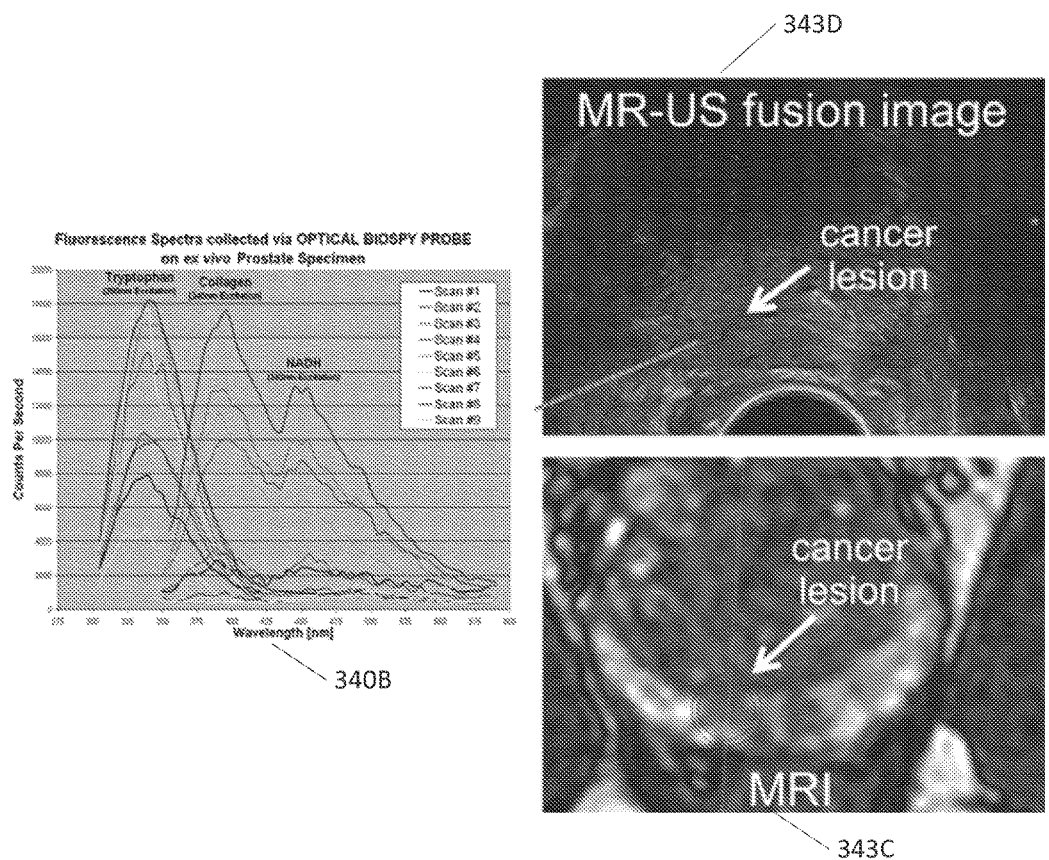
FIG. 25 illustrates two photographs on the right side, the bottom photo is an MRI image where a cancer lesion was first diagnosed by a radiologist and the upper photo is a MRI fusion image showing a cancer lesion fused with an ultrasound (US) image.

As another example, FIG. 25 illustrates two photographs on the right side, the bottom right photo 343C is an MRI image where a cancer lesion was first diagnosed by a radiologist and the upper right photo 343D is a MRI fusion image showing a cancer lesion fused with an ultrasound (US) image. This combined MRI/US fusion image can be used for transrectal or transperineal directed biopsy of the prostate. When an optical biopsy needle 334 is used, an additional fluorescence spectra can be generated in the computer monitor display 340 from the location or vicinity of the cancer lesion shown in MRI/US fusion image. FIG. 25 illustrates one photograph 340B on the left side which illustrates fluorescence spectra. This fluorescence spectra presented on display 340 when processed by a tissue classification algorithm can either confirm or contradict the existence of a cancer lesion shown in MRI/US fusion image 343D.

For example, a system for use with a tissue to create a fused image includes the an optical probe array 74 in combination with a MRI or CT imaging guidance system 141 for identifying the position of the optical probes relative to the tissue. In addition, an ultrasound imaging guidance system 114 identifies the position of the optical probes relative to the tissue. A three-dimensional user interface imaging system 116 generates a three-dimensional image of the tissue based on the generated light signals and the identified position of the optical probes 74 as indicated by the MRI imaging guidance system 141 and as indicated by the ultrasound imaging guidance system 114. The resulting images as shown in FIGS. 24-25 are a fusion of an MRI (or CT) image provided by the MRI (or CT) imaging guidance system 141 and an ultrasound image provided by the ultrasound imaging guidance system 114. As noted herein, MR, CT, or fusion images can be used to guide prostate biopsies to cancer lesions identified by the radiologists. The optical biopsy needle 134 provides additional information by elastic scattering spectra or fluorescence spectra or both. This information after processed by a tissue classification algorithm indicates whether a cancer lesion shown by the images indeed is cancer or not.

Thus, in one form, a system as shown in FIG. 10 is for use with a tissue. An optical probe array system 112, 115 has at least two or more optical probes for inserting into the tissue, for illuminating the tissue and for generating light signals corresponding to the illuminated tissue. An imaging system 116, 117 generates an image of the tissue based on the generated light signals.

Thus, in another form, a system as shown in FIG. 10 is for use with a tissue. An optical probe array system 112, 115 has at least two or more optical probes for inserting into the tissue, for illuminating the tissue and for generating light signals corresponding to the illuminated tissue. An imaging system 114, 116, 117 generates an image of the tissue based on the generated light signals.

Thus, in another form, a system as shown in FIG. 13 is for use with a tissue 138. An optical probe array system 132 has at least two or more optical probes 134 for inserting into the tissue, for illuminating the tissue 138 and for generating light signals corresponding to the illuminated tissue. An imaging system 136, 140 generates an image of the tissue based on the generated light signals.

Thus, in another form, a system as shown in FIG. 23 is for use with a tissue 338. An optical probe array system 332 has at least two or more optical probes 334 for inserting into the tissue, for illuminating the tissue 338 and for generating light signals corresponding to the illuminated tissue. An imaging system 336, 340, 341, 343 generates an image of the tissue based on the generated light signals.

Thus, in another form, a system as shown in FIG. 23 is for use with a tissue 338. An optical probe array system 332 has at least two or more optical probes 334 for inserting into the tissue, for illuminating the tissue 338 and for generating light signals corresponding to the illuminated tissue. An imaging system 336, 340 generates an image of the tissue based on the generated light signals.

Thus, in another form, a system as shown in FIG. 23 is for use with a tissue 338. An optical probe array system 332 has at least two or more optical probes 334 for illuminating the tissue 338 and for generating light signals corresponding to the illuminated tissue fluorescence and/or corresponding to the illuminated tissue diffuse reflectance spectroscopy for distinguishing between cancer tissue and non-cancer tissue. A controller 336 and display 340 generate an image corresponding to the generated light signals. An MRI or CT image indicative of the position of the optical probes relative to the tissue (stored on a storage device) is generated by an imaging system 341. An ultrasound imaging guidance system for identifying the position of the optical probes relative to the tissue is part of the imaging system 341. The imaging system 341 generates an image (see photograph 343B, 343D) of the tissue on display 343 based on the identified position of the optical probes 334 as indicated by the MRI or CT imaging guidance system 341 and as indicated by the ultrasound imaging guidance system. The generated image is a fusion of an MRI or CT image provided by the MRI or CT imaging guidance system and an ultrasound image provided by the ultrasound imaging guidance system. A treatment device 339 employing a treatment modality such as described herein can be used in combination with the imaged and/or mapped tissue to treat the imaged tissue. For example, the device 139 can be a Cryotherapy device; a Photodynamic Therapy device; a Brachytherapy device; a high-intensity focused ultrasound (HIFU) device; a tissue ablation device; a Laser ablation device; a RF ablation device; a Vapor ablation device; and a Local drug delivery device.

In summary of one embodiment, a physician will introduce the optical probe under imaging guidance (e.g. ultrasound, MRI, CT) into specific regions of the prostate using a spatial template. The physician will then systematically perform an optical sampling of the prostate to create a 3-D mapping of the prostate where both benign and malignant sites are identified and recorded. With this 3-D mapping the physician can then return to the malignant sites and deploy therapeutic modalities. Optionally, other images from systems such as MRI and CT scans combined with TRUS image (Image fusion of TRUS and MRI or TRUS and CT) can be communicated into the fluorometer and overlapped with optical measurements.

The measurement points where the tissue classification algorithm has classified as abnormal may be displayed with a different color than the normal tissue. The location of the abnormal tissue with respect to transrectal ultrasound system may also be provided by the optical system so the physician can easily locate the abnormal tissue under ultrasound and deliver therapy to the appropriate location.

Design and Materials

The optical probe is an elongated hypodermic needle with a fiber optic bundle passing through an internal bore. The fiber optic bundle is comprised of at least one transmitter fiber and at least one receiver fiber to form an optical sensor(s). The needle is capable of accommodating optical sensors both at the distal tip and various positions along its length. The transmitter fiber optics transmit light from a light source or light sources (e.g. light-emitting diode or laser) to the tissue under examination. Multiple light sources may be routed to the fibers either individually or simultaneously by way of optical guides (e.g. focusing lenses or mirrors). The receiver fiber optics transmit light reflected from or subsequently emitted by the tissue under examination to at least one detector or sensor. The light sources and light detector are controlled by computer or similar electronic control that comprises a microprocessor, storage, display, and graphical user interface (GUI). Signals generated by the detector are processed through a diagnostic algorithm and stored.

The component for generating the 3-D diagnostic mapping couples diagnostic information from the spectroscopic evaluation with the spatial location of the respective optical sensors at the time of acquisition. The 3-D mapping system comprises a computer with graphical display, graphical user interface, and software that integrates inputs from the diagnostic algorithm and the imaging system (e.g. ultrasound or MRI).

In one embodiment, a physician will introduce the optical probe under imaging guidance (e.g. ultrasound, MRI) into specific regions of the prostate using a spatial template. The physician will then systematically perform an optical sampling of the prostate to create a 3-D mapping of the prostate where both benign and malignant sites are identified and recorded. With this 3-D mapping the physician can then return to the malignant sites and deploy therapeutic modalities. For example, the physician would insert a 2×2 probe and the system would sequentially excite each of the optical sensors in order to determine the configuration of tissue adjacent to, contiguous to and/or in contact with the probes. The system knows the position of each sensor relative to each other and relative to the tissue (based on the USP) and would store the resulting information. Next, the physician would re-insert the probe at a different, adjacent location and the excitation and measuring process would be repeated. Additional insertions may be needed until the tissue of insert is measured and a complete 3-D map is generated.

Integrated 3-D Mapping and Therapy System

The 3-D mapping system can be used with all therapeutic modalities to diagnose and treat prostate cancer patients. The system initially optically maps the prostate and identifies the locals of the abnormal tissue. Either using the same probe with optical sensors or another probe, any of the therapies, such as the mentioned in therapy section of this application (or others), may be applied.

The summary is provided to help the reader quickly ascertain the nature of the technical disclosure. They are submitted with the understanding that they will not be used to interpret or limit the scope or meaning of the claims. The summary is provided to introduce a selection of concepts in simplified form that are further described in the Detailed Description. The summary is not intended to identify key features or essential features of the claimed subject matter, nor is it intended to be used as an aid in determining the claimed subject matter.

For purposes of illustration, programs and other executable program components, such as the operating system, are illustrated herein as discrete blocks. It is recognized, however, that such programs and components reside at various times in different storage components of a computing device, and are executed by a data processor(s) of the device.

Although described in connection with an exemplary computing system environment, embodiments are operational with numerous other general purpose or special purpose computing system environments or configurations. The computing system environment is not intended to suggest any limitation as to the scope of use or functionality of any aspect of the invention. Moreover, the computing system environment should not be interpreted as having any dependency or requirement relating to any one or combination of components illustrated in the exemplary operating environment. Examples of well-known computing systems, environments, and/or configurations that may be suitable for use with aspects of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the invention may also be practiced in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the invention.

Embodiments may be implemented with processor-executable instructions. The processor-executable instructions may be organized into one or more processor-executable components or modules on a tangible processor readable storage medium. Aspects of the invention may be implemented with any number and organization of such components or modules. For example, aspects of the invention are not limited to the specific processor-executable instructions or the specific components or modules illustrated in the figures and described herein. Other embodiments may include different processor-executable instructions or components having more or less functionality than illustrated and described herein.

The order of execution or performance of the operations in embodiments illustrated and described herein is not essential, unless otherwise specified. That is, the operations may be performed in any order, unless otherwise specified, and embodiments may include additional or fewer operations than those disclosed herein. For example, it is contemplated that executing or performing a particular operation before, contemporaneously with, or after another operation is within the scope of aspects of the invention.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the invention are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the invention by way of example and not by way of limitation. This description enables one skilled in the art to make and use the invention, and describes several embodiments, adaptations, variations, alternatives and uses of the invention, including what is presently believed to be the best mode of carrying out the invention. Additionally, it is to be understood that the invention is not limited in its application to the details of construction and the arrangement of components set forth in the following description or illustrated in the drawings. The invention is capable of other embodiments and of being practiced or carried out in various ways. Also, it will be understood that the phraseology and terminology used herein is for the purpose of description and should not be regarded as limiting.

Having described aspects of the invention in detail, it will be apparent that modifications and variations are possible without departing from the scope of aspects of the invention as defined in the appended claims. It is contemplated that various changes could be made in the above constructions, products, and methods without departing from the scope of aspects of the invention. In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A system evaluating tissue comprising:
   an optical probe array system having at least one or more optical probes configured to insert into an interior of the tissue, said optical probe comprising:
   at least one light source configured to illuminate a portion of the interior tissue adjacent to, contiguous to and/or in contact with the optical probe at a location within the tissue and configured to generate from the portion of the interior tissue light signals fluoresced or elastically scattered from the illuminated interior tissue, said fluoresced or scattered light signals comprising Auto-Fluorescence Spectra (AFS) or Elastic Scattering Spectra (ESS);

an optical sensor configured to capture the AFS or ESS signals indicative of the AFS or ESS of the illuminated interior tissue; and a tissue characterization imaging system comprising a spectroscope configured to evaluate the AFS or ESS signals captured by the optical sensor based on a fluorescence or elastic scattering of the captured signals, said tissue characterization imaging system executing an algorithm analyzing selected data of the AFS or ESS signals to generate a diagnostic classification indicative of tissue condition of the illuminated interior tissue based only on the selected data, said tissue characterization imaging system configured to provide the classification by correlating the location of the classified interior tissue to a three-dimensional image of the tissue, and generating a three-dimensional optical spectroscopic image showing the location and classification of the illuminated interior tissue in relation to the three-dimensional image of the tissue.

2. The system of claim 1 further comprising an imaging guidance system for identifying a position of the one or more optical probes relative to the tissue, wherein the imaging guidance system comprises a three-dimensional imaging system for generating the three-dimensional image of the tissue.

3. The system of claim 2, wherein the imaging guidance system comprises an ultrasound imaging system.

4. The system of claim 2, wherein the imaging guidance system comprises an MRI or CT imaging system.

5. The system of claim 1 further comprising a treatment device for treating the illuminated interior tissue, wherein the treatment device for treating the illuminated interior tissue comprises at least one of the following:
 a Cryotherapy device;
 a Photodynamic Therapy device;
 a Brachytherapy device;
 a high-intensity focused ultrasound (HIFU) device;
 a tissue ablation device;
 a Laser ablation device;
 a RF ablation device;
 a Vapor ablation device;
 a Local drug delivery device.

6. The system of claim 1 further comprising a grid or template for aligning the one or more optical probes into a predetermined orientation relative to each other and relative to the tissue.

7. The system of claim 1 wherein the optical probe comprises:
 a shaft;
 at least one pair of optical devices supported by the shaft, each pair of optical devices comprising:
  the at least one light source and
  the optical sensor; and
 transmit and receive optical fibers within the shaft for transmitting light to illuminate the portion of the interior tissue and for receiving the fluoresced light signals from the illuminated interior tissue to the optical sensor.

8. The system as in claim 7, wherein the at least one light source comprises multiple light sources routed to the transmit optical fiber by optical guides.

9. The system of claim 1 wherein the tissue characterization imaging system further comprises:
 an MRI or CT imaging guidance system generating an MM or CT image indicative of a position of the one or more optical probes relative to the tissue;
 an ultrasound imaging guidance system for generating an ultrasound image identifying the position of the one or more optical probes relative to the tissue; and
 wherein the three-dimensional image of the tissue comprises a fused image of the tissue based on the identified position of the one or more optical probes as indicated by the MM or CT imaging guidance system and as indicated by the ultrasound imaging guidance system wherein the fused image is a fusion of the MM or CT image and the ultrasound image.

10. The system of claim 1 wherein the spectroscope is configured for evaluating diffuse reflectance of the generated light signals and wherein the algorithm utilizes selected data of the evaluated diffuse reflectance to generate the diagnostic classification indicative of tissue condition.

11. The system of claim 1 further comprising an MM or CT imaging guidance system generating an MRI or CT image indicative of a position of the one or more optical probes relative to the tissue prior to the tissue characterization imaging system evaluating the captured signals.

12. The system of claim 5 further comprising interstitial thermo-sensors for monitoring the temperature of the tissue during treatment.

13. The system of claim 1, wherein the diagnostic classification indicative of tissue condition comprises benign, malignant, abnormal, cancer, disease or calcified.

14. The system as in claim 13, wherein the diagnostic classification indicative of tissue condition comprises benign and wherein the three-dimensional optical spectroscopic image shows the location and benign classification of the illuminated interior tissue in relation to the three-dimensional image of the tissue.

15. The system as in claim 13, wherein the diagnostic classification indicative of tissue condition comprises abnormal and wherein the three-dimensional optical spectroscopic image shows the location and abnormal classification of the illuminated interior tissue as a different color than normal tissue.

16. The system of claim 1, wherein the tissue comprises prostate tissue.

17. The system of claim 1, wherein the fluoresced light signals are fluoresced from endogenous fluorophores within the illuminated interior tissue and wherein the spectroscope is configured to evaluate the AFS signals captured by the optical sensor based on an isolated fluorescence of at least one endogenous fluorophore, said tissue characterization imaging system executing an algorithm analyzing selected data of the isolated fluorescence of the at least one endogenous fluorophore to generate the diagnostic classification indicative of tissue condition of the illuminated interior tissue based at least on the selected data of the isolated fluorescence of the at least one endogenous fluorophore.

18. The system of claim 17, wherein the at least one endogenous fluorophore comprises NADH, tryptophan, and/or collagen.

19. The system of claim 18, wherein the at least one endogenous fluorophore comprises tryptophan, tyrosine, phenylalanine, collagen, elastin, FAD, flavin, NADH, NADPH, Vitamin A, Vitamin K, Vitamin D, pyridoxine, pyridoxamone, pyridoxal, pyridoxic acid, pyridoxal 5'-phosphate, Vitamin B12, phospholipid, lipofuscin, ceroid, and/or porphyrin.

20. The system of claim 17, wherein the at least one light source provides an excitation light at 290 nm and the at least one endogenous fluorophore from which fluorescence is isolated comprises tryptophan.

21. The system of claim 17, wherein the at least one light source provides an excitation light at 350-370 nm and the at least one endogenous fluorophore from which fluorescence is isolated comprises NADH.

22. The system of claim 17, wherein the at least one light source provides an excitation light at 340 nm.

23. The system of claim 17, wherein
the at least one light source is configured to generate from the portion of the interior tissue light signals fluoresced and elastically scattered from the illuminated interior tissue said fluoresced and scattered light signals comprising Auto-Fluorescence Spectra (AFS) and Elastic Scattering Spectra (ESS);
the optical sensor is configured to capture the AFS and ESS signals indicative of the AFS and ESS of the illuminated interior tissue; and
wherein the algorithm to generate the diagnostic classification indicative of tissue condition of the illuminated interior tissue is based on the selected data of the fluorescence of the at least one endogenous fluorophore in combination with selected data of the ESS signals.

24. The system of claim 23, wherein the at least one light source has a wavelength range of at least 350 nm to 1200 nm and absorption features are provided at least at approximately 425 nm and 650 nm for use in diagnostic classification.

25. The system of claim 23, wherein the at least one light source has a wavelength range of at least 350 nm to 700 nm and absorption features are provided at approximately 425 nm and 650 nm for use in diagnostic classification.

26. The system of claim 23, wherein the tissue comprises prostate tissue and the diagnostic classification indicative of tissue condition comprises high grade disease or low grade disease based on Gleason rating.

27. The system of claim 1, wherein the three-dimensional optical spectroscopic image provides tumor volume estimates.

28. The system of claim 1, wherein the three-dimensional optical spectroscopic image provides distribution of disease within the tissue.

29. The system of claim 1, wherein the three-dimensional optical spectroscopic image shows the classification by a color indicating the tissue condition.

30. The system of claim 1, wherein the system includes a user interface allowing a user to select an image variation of the three-dimensional optical spectroscopic image including a two-dimensional image, a fused image, a black and white image, a color image, or a line image.

31. The system of claim 1, wherein the optical probe further comprises a mechanism configured for obtaining a biopsy of the illuminated interior tissue while the optical probe is in position for illuminating the portion of the interior tissue.

32. The system of claim 1, wherein the optical probe further comprises a mechanism configured for delivering a therapeutic modality to the illuminated interior tissue while the optical probe is in position for illuminating the portion of the interior tissue, wherein the therapeutic modality comprises at least one of the following:
Cryotherapy;
Photodynamic Therapy;
Brachytherapy;
high-intensity focused ultrasound (HIFU);
tissue ablation;
Laser ablation;
RF ablation;
Vapor ablation;
Local drug delivery.

33. The system of claim 32, wherein the diagnostic classification comprises malignant and wherein the mechanism is configured to provide focused targeted delivery of the therapeutic modality to the illuminated interior tissue classified as malignant while avoiding other tissue.

* * * * *